(12) United States Patent
Hayakawa

(10) Patent No.: US 11,667,505 B2
(45) Date of Patent: Jun. 6, 2023

(54) ASEPTIC FILLING MACHINE AND ASEPTIC FILLING METHOD

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 658 days.

(21) Appl. No.: 16/611,313

(22) PCT Filed: May 8, 2018

(86) PCT No.: PCT/JP2018/017825
§ 371 (c)(1),
(2) Date: Nov. 6, 2019

(87) PCT Pub. No.: WO2018/207787
PCT Pub. Date: Nov. 15, 2018

(65) Prior Publication Data
US 2020/0165115 A1    May 28, 2020

(30) Foreign Application Priority Data

May 10, 2017  (JP) .............................. JP2017-093763
May 17, 2017  (JP) .............................. JP2017-097966

(51) Int. Cl.
*A61L 2/00* (2006.01)
*B01J 19/08* (2006.01)
(Continued)

(52) U.S. Cl.
CPC .............. *B67C 7/0073* (2013.01); *A61L 2/06* (2013.01); *A61L 2/087* (2013.01); *A61L 2/10* (2013.01);
(Continued)

(58) Field of Classification Search
CPC ..... A61L 2/04; A61L 2/07; A61L 2/08; A61L 2/10; F04F 5/48; B29C 49/06; B65B 55/10; B67C 7/00
(Continued)

(56) References Cited

U.S. PATENT DOCUMENTS 6,562,281 B1    5/2003  Marchau et al.
2009/0218733 A1  9/2009  Andison et al.
(Continued)

FOREIGN PATENT DOCUMENTS

CN    101391736 A    3/2009
EP    2 578 504 A1   4/2013
(Continued)

OTHER PUBLICATIONS

Japanese Office Action (Application No. 2017-093763) dated Dec. 14, 2021 (with English translation).
(Continued)

*Primary Examiner* — Monzer R Chorbaji
(74) *Attorney, Agent, or Firm* — Burr Patent Law, PLLC

(57) ABSTRACT

An aseptic filling machine capable of performing molding and filling at the same time that has a compact facility size, requires a reduced initial investment, requires a reduced running cost because of its simplified process, and ensures an aseptic condition with reliability, and an aseptic filling method therefor. An aseptic filling machine includes a pre-heating sterilizing portion that sterilizes a preform, a heating portion that heats the sterilized preform, a molding and filling portion that fills the heated preform with a sterilized content under high pressure, thereby molding the preform into a bottle and at the same time filling the preform with the content, and a sealing portion that seals the bottle filled with the content. Before the aseptic filling machine starts operating, each portion is sterilized. During operation
(Continued)

of the aseptic filling machine, aseptic air is supplied to each portion to maintain the aseptic condition.

47 Claims, 12 Drawing Sheets

(51) Int. Cl.
*B67C 7/00* (2006.01)
*A61L 2/06* (2006.01)
*A61L 2/08* (2006.01)
*A61L 2/10* (2006.01)
*A61L 2/20* (2006.01)
*A61L 2/26* (2006.01)
*B29C 49/46* (2006.01)
*B67C 3/22* (2006.01)
*B29L 31/00* (2006.01)

(52) U.S. Cl.
CPC ............... *A61L 2/208* (2013.01); *A61L 2/26* (2013.01); *B29C 49/46* (2013.01); *B67C 3/22* (2013.01); *A61L 2202/122* (2013.01); *A61L 2202/17* (2013.01); *A61L 2202/182* (2013.01); *A61L 2202/23* (2013.01); *B29C 2049/4635* (2013.01); *B29C 2049/4664* (2013.01); *B29L 2031/7158* (2013.01); *B67C 2003/227* (2013.01); *B67C 2003/228* (2013.01)

(58) Field of Classification Search
USPC ............... 422/24, 28, 186.05, 292, 302, 307
See application file for complete search history.

(56) References Cited

U.S. PATENT DOCUMENTS

| | | |
|---|---|---|
| 2011/0037188 A1 | 2/2011 | Hirdina |
| 2011/0094616 A1 | 4/2011 | Hayakawa et al. |
| 2015/0284115 A1 | 10/2015 | Voth et al. |
| 2016/0053777 A1* | 2/2016 | Winzinger ............ B65B 31/022 417/54 |
| 2018/0001541 A1 | 1/2018 | Hayakawa |
| 2018/0009646 A1 | 1/2018 | Hayakawa et al. |
| 2018/0208446 A1 | 7/2018 | Hayakawa et al. |
| 2019/0127197 A1 | 5/2019 | Hayakawa et al. |

FOREIGN PATENT DOCUMENTS

| | | |
|---|---|---|
| EP | 2 987 620 A1 | 2/2016 |
| JP | H05-310222 A1 | 11/1993 |
| JP | H11-091877 A | 4/1999 |
| JP | 2000-043129 A1 | 2/2000 |
| JP | 2001-510104 A1 | 7/2001 |
| JP | 2006-111295 A1 | 4/2006 |
| JP | 2009-274740 A1 | 11/2009 |
| JP | 2010-155631 A1 | 7/2010 |
| JP | 2011-042169 A1 | 3/2011 |
| JP | 2011-506130 A1 | 3/2011 |
| JP | 2014-051304 A1 | 3/2014 |
| JP | 5582213 | 9/2014 |
| JP | 2015-199547 A1 | 11/2015 |
| WO | 2009/075791 A1 | 6/2009 |
| WO | 2014/209341 A1 | 12/2014 |
| WO | 2014/209356 A1 | 12/2014 |
| WO | 2016/104410 A1 | 6/2016 |
| WO | 2016/143772 A1 | 9/2016 |
| WO | 2017/047691 A1 | 3/2017 |

OTHER PUBLICATIONS

International Search Report and Written Opinion (Application No. PCT/JP2018/017825) dated Aug. 7, 2018.
Extended European Search Report (Application No. 18798293.9) dated Mar. 5, 2021.
Japanese Office Action (with English translation), Japanese Application No. 2017-093763, dated Jun. 28, 2022 (10 pages).
European Office Action dated Mar. 20, 2023 (Application No. 18 798 293.9).

* cited by examiner

SUPPLY OF PREFORM

BLASTING OF STERILIZER GAS

ASEPTIC FILLING MACHINE AND ASEPTIC FILLING METHOD

CROSS-REFERENCE TO RELATED APPLICATIONS

This application is the National Stage entry of International Application No. PCT/JP2018/017825 filed on May 8, 2018, which designated the United States, and claims the benefit under 35 U.S.C. § 119(a)-(d) of Japanese Patent Application No. 2017-093763 filed on May 10, 2017, and Japanese Parent Application No. 2017-097966 filed on May 17, 7017.

TECHNICAL FIELD

The present invention relates to an aseptic filling machine that sterilizes a preform, and then molds the sterilized preform in an aseptic atmosphere and at the same time fills the preform with a content, and an aseptic filling method therefor.

BACKGROUND ART

Teas, sports drinks, milk drinks, juice drinks and other drinks are mostly shipped in a biaxially oriented polyethylene terephthalate (PET) bottle. These drinks may become rotten if they are contaminated with bacteria or the like during charging. To avoid this, a sterilized bottle is filled with a sterilized drink in an aseptic atmosphere and sealed with a sterilized cap. The process from molding of a preform into a bottle to sealing of the bottle is continuously performed by a single aseptic filling machine.

As such aseptic filling machines, in-line systems have been proposed which produce an aseptic package by conveying a preform, blasting a sterilizer such as hydrogen peroxide to the preform during conveyance, heating the preform to activate the sterilizer on the surface of the preform and at the same time to raise the temperature of the preform to a molding temperature, molding the heated preform into a bottle in a blow molding machine, filling the molded bottle with a drink or the like, and capping the bottle (Patent Literatures 1 and 2).

Furthermore, aseptic filling machines have also been proposed which heat a preform to a molding temperature, mold the heated preform into a container, sterilize the molded container, fill the sterilized container with a sterilized content in an aseptic atmosphere, and seal the container filled with the content with a sterilized lid member (Patent Literatures 3 and 4).

The aseptic filling machines described above, which mold a preform into a bottle and fill the molded bottle with a content, are long and large systems. To overcome this disadvantage, it has been proposed to perform molding and filling at the same time by filling a preform with a drink to be a content under high pressure instead of a high-pressure gas used to blow-mold the preform (Patent Literatures 5 and 6).

According to the method described in Patent Literature 5, an extension rod or inner pipe is incorporated in a core of a mold used for injection molding of a preform, the preform formed on the exterior of the core by injection molding is introduced into the mold, and the introduced preform is molded and at the same time filled, so that the aseptic condition of the preform can be maintained. The method is extremely complicated in that successive injection moldings are performed, and the core used for the injection moldings is also used for blow moldings.

According to the method disclosed in Patent Literature 6, a preform is sterilized with vapor or the like, the sterilized preform is heated, and a liquid commodity is fed into the heated preform under high pressure, thereby molding the preform into a bottle and at the same time filling the bottle with the liquid commodity. In order to produce an aseptic product by feeding a liquid commodity at room temperature, the process needs to be performed in an aseptic atmosphere, and thus the cost is high. In addition, when the bottle is filled at room temperature, the aseptic condition cannot be adequately ensured because bacteria or other contaminants can escape through the contamination prevention device in operation to contaminate the product at any time.

CITATION LIST

Patent Literature

Patent Literature 1
Japanese Patent Laid-Open No. 2001-510104 Patent Literature 2
Japanese Patent Laid-Open No. 2009-274740 Patent Literature 3
Japanese Patent Laid-Open No. 2006-111295 Patent Literature 4
Japanese Patent Laid-Open No. 2010-155631 Patent Literature 5
Japanese Patent Laid-Open No. 2000-43129 Patent Literature 6 Japanese Patent Laid-Open No. 2011-506130

SUMMARY OF INVENTION

Technical Problem

Conventional aseptic filling machines for a bottle mold a preform into a bottle and sterilize the molded bottle. Such machines require a large amount of sterilizer and are large in size, so that aseptic filling machines that sterilize a preform yet to be molded are becoming popular. However, such aseptic filling machines, which sterilize a preform, mold the sterilized preform into a bottle and fill the molded bottle with a content, are still large in size, although the overall size thereof is smaller than that of the aseptic filling machines that sterilize molded bottles.

To overcome the disadvantage, as disclosed in Patent Literatures 5 and 6, it has been proposed to perform molding of a preform into a bottle and filling with a drink by filling a sterilized preform with a drink to be a content under high pressure. However, there has not been an appropriate method of maintaining the aseptic condition throughout the process of molding a sterilized preform into a bottle and filling the molded bottle with a drink. The preform once sterilized can be contaminated with bacteria or the like before filling performed at the same time as molding, and filling at high temperature is recommended in Patent Literature 6. If filling is performed at high temperature, even when the inner surface of the preform is contaminated with bacteria or the like, the bacteria or the like is killed by the heat of the content that is to fill the preform. However, the product filled at high temperature and sealed needs to be cooled after that, and the content deteriorates in quality because of the heating, so that the advantages of the aseptic filling are reduced.

According to Patent Literature 5, a preform is molded into a bottle and at the same time filled with a content while the preform is fitted on the core used for injection molding, thereby maintaining the aseptic condition. However, the process is complicated, and it is difficult to achieve high-speed productivity.

There is a demand for an aseptic filling machine capable of performing molding and filling at the same time that has a compact facility size, requires a reduced initial investment, requires a reduced running cost because of its simplified process, and ensures an aseptic condition with reliability. The present invention has been devised to solve the problems described above, and an object of the present invention is to provide an aseptic filling machine capable of molding of a preform into a bottle and filling of the preform at the same time by filling a sterilized preform with a sterilized content under high pressure while maintaining the aseptic condition of the sterilized preform, and an aseptic filling method therefor.

Solution to Problem

An aseptic filling machine according to the present invention is an aseptic filling machine, comprising a pre-heating sterilizing portion that sterilizes a preform, a heating portion that heats the sterilized preform, a molding and filling portion that fills the heated preform with a sterilized content under high pressure, thereby molding the preform into a bottle and at the same time filling the preform with the content, and a sealing portion that seals the bottle filled with the content, wherein the pre-heating sterilizing portion, the heating portion, the molding and filling portion and the sealing portion are each shielded by a chamber, a sterilizing apparatus and an aseptic air supplying apparatus are provided, and of a pre-heating sterilizing portion chamber that shields the pre-heating sterilizing portion, a heating portion chamber that shields the heating portion, a molding and filling portion chamber that shields the molding and filling portion and a sealing portion chamber that shields the sealing portion, the sterilizing apparatus sterilizes an interior and an inner surface of at least the molding and filling portion chamber and the sealing portion chamber, and the aseptic air supplying apparatus supplies aseptic air into at least the molding and filling portion chamber and the sealing portion chamber.

An aseptic filling machine according to the present invention is an aseptic filling machine, comprising a heating portion that heats a preform, a post-heating sterilizing portion that sterilizes the heated preform, a molding and filling portion that fills the sterilized preform with a sterilized content under high pressure, thereby molding the preform into a bottle, and a sealing portion that seals the bottle filled with the content, wherein the post-heating sterilizing portion, the molding and filling portion and the sealing portion are each shielded by a chamber, a sterilizing apparatus and an aseptic air supplying apparatus are provided, and of a post-heating sterilizing portion chamber that shields the post-heating sterilizing portion, a molding and filling portion chamber that shields the molding and filling portion and a sealing portion chamber that shields the sealing portion, the sterilizing apparatus sterilizes an interior and an inner surface of at least the molding and filling portion chamber and the sealing portion chamber, and the aseptic air supplying apparatus supplies aseptic air into at least the molding and filling portion chamber and the sealing portion chamber.

An aseptic filling machine according to the present invention is an aseptic filling machine, comprising a pre-heating sterilizing portion that sterilizes a preform, a heating portion that heats the sterilized preform, a post-heating sterilizing portion that sterilizes the heated preform, a molding and filling portion that fills the heated preform with a sterilized content under high pressure, thereby molding the preform into a bottle and at the same time filling the preform with the content, and a sealing portion that seals the bottle filled with the content, wherein the pre-heating sterilizing portion, the heating portion, the post-heating sterilizing portion, the molding and filling portion and the sealing portion are each shielded by a chamber, a sterilizing apparatus and an aseptic air supplying apparatus are provided, and of a pre-heating sterilizing portion chamber that shields the pre-heating sterilizing portion, a heating portion chamber that shields the heating portion, a post-heating sterilizing portion chamber that shields the post-heating sterilizing portion, a molding and filling portion chamber that shields the molding and filling portion and a sealing portion chamber that shields the sealing portion, the sterilizing apparatus sterilizes an interior and an inner surface of at least the molding and filling portion chamber and the sealing portion chamber, and the aseptic air supplying apparatus supplies aseptic air into at least the molding and filling portion chamber and the sealing portion chamber.

Further, in the aseptic filling machine according to the present invention, preferably, a cleaning apparatus is provided which cleans the interior of the molding and filling portion chamber and the sealing portion chamber.

Further, in the aseptic filling machine according to the present invention, preferably, the molding and filling portion chamber includes a movable portion that holds the molding and filling portion and a fixed portion that shields the molding and filling portion from an outside air.

Further, in the aseptic filling machine according to the present invention, preferably, a sterilizing device for the preform in the pre-heating sterilizing portion is configured to do any one or more of contact of the preform with a sterilizer, irradiation of the preform with an electron beam, irradiation of the preform with light containing ultraviolet radiation, contact of the preform with hot water, and contact of the preform with overheated vapor.

Further, in the aseptic filling machine according to the present invention, preferably, a sterilizing device for the preform in the post-heating sterilizing portion is configured to do any one or more of contact of the preform with a gas or mist of a sterilizer or a mixture thereof, irradiation of the preform with an electron beam, irradiation of the preform with light containing ultraviolet radiation, and contact of the preform with overheated vapor.

Further, in the aseptic filling machine according to the present invention, preferably, the molding and filling portion includes at least a mold, a blow nozzle, an extension rod, a valve block and a pressure apparatus that pressurizes the content.

Further, in the aseptic filling machine according to the present invention, preferably, the pressure apparatus is a high-pressure plunger pump.

Further, in the aseptic filling machine according to the present invention, preferably, a cup-shaped closure apparatus that receives a substance discharged from the blow nozzle is provided.

Further, in the aseptic filling machine according to the present invention, preferably, an extension rod shielding chamber that shields the extension rod is provided.

Further, in the aseptic filling machine according to the present invention, preferably, an extension rod driving apparatus is provided which drives the extension rod to a position where the extension rod is not inserted in the blow nozzle.

An aseptic filling method according to the present invention is an aseptic filling method, comprising a pre-heating sterilization step of sterilizing a preform, a heating step of heating the sterilized preform, a molding and filling step of filling the heated preform with a sterilized content under high pressure, thereby molding the preform into a bottle and at the same time filling the preform with the content, and a sealing step of sealing the bottle filled with the content, wherein an interior and an inner surface of at least a chamber that shields from outside a portion in which the molding and filling step is performed and a chamber that shields from outside a portion in which the sealing step is performed are sterilized, aseptic air is supplied into the chambers, an aseptic condition is maintained in the chambers, and at least the molding and filling step and the sealing step are performed in the respective chambers in which the aseptic condition is maintained.

An aseptic filling method according to the present invention is an aseptic filling method, comprising a heating step of heating a preform, a post-heating sterilization step of sterilizing the heated preform, a molding and filling step of filling the sterilized preform with a sterilized content under high pressure, thereby molding the preform into a bottle and at the same time filling the bottle with the content, and a sealing step of sealing the bottle filled with the content, wherein an interior and an inner surface of a chamber that shields from outside a portion in which the molding and filling step is performed and a chamber that shields from outside a portion in which the sealing step is performed are sterilized, aseptic air is supplied into the chambers, an aseptic condition is maintained in the chambers, and the molding and filling step and the sealing step are performed in the respective chambers in which the aseptic condition is maintained.

An aseptic filling method according to the present invention is an aseptic filling method, comprising a pre-heating sterilization step of sterilizing a preform, a heating step of heating the preform, a post-heating sterilization step of sterilizing the heated preform, a molding and filling step of filling the sterilized preform with a sterilized content under high pressure, thereby molding the preform into a bottle and at the same time filling the bottle with the content, and a sealing step of sealing the bottle filled with the content, wherein an interior and an inner surface of a chamber that shields from outside a portion in which the molding and filling step is performed and a chamber that shields from outside a portion in which the sealing step is performed are sterilized, aseptic air is supplied into the chambers, an aseptic condition is maintained in the chambers, and the molding and filling step and the sealing step are performed in the respective chambers in which the aseptic condition is maintained.

Further, in the aseptic filling method according to the present invention, preferably, before the interior and the inner surface of the chambers in which the molding and filling step and the sealing step are performed are sterilized, the interior and the inner surface of the chambers are cleaned.

Further, in the aseptic filling method according to the present invention, preferably, the pre-heating sterilization step is achieved by any one or more of contact of the preform with a sterilizer, irradiation of the preform with an electron beam, irradiation of the preform with light containing ultraviolet radiation, contact of the preform with hot water, and contact of the preform with overheated vapor.

Further, in the aseptic filling method according to the present invention, preferably, the post-heating sterilization step is achieved by any one or more of contact of the preform with a gas or mist of a sterilizer or a mixture thereof, irradiation of the preform with an electron beam, irradiation of the preform with light containing ultraviolet radiation, and contact of the preform with overheated vapor.

Further, in the aseptic filling method according to the present invention, preferably, the molding and filling step includes connecting a blow nozzle to a top of a mouth portion of the sterilized and heated preform, closing a mold, expanding the preform in a lengthwise direction with an extension rod and then introducing the content pressurized into the preform under the control of a valve block, expanding the preform in a crosswise direction to mold the preform into the bottle having a shape of the mold, and at the same time filling the preform with the content to close to a lower end of the mouth portion of the preform.

Further, in the aseptic filling method according to the present invention, preferably, a discharge port of the blow nozzle is closed by a cup-shaped closure apparatus, and a discharged substance is received by the cup-shaped closure apparatus and circulated, thereby cleaning and sterilizing an interior of piping for the content.

Further, in the aseptic filling method according to the present invention, preferably, the interior of the chamber in which the molding and filling step is performed is sterilized in a state where the extension rod is not inserted in the blow nozzle.

Further, in the aseptic filling method according to the present invention, preferably, the interior of the chamber in which the molding and filling step is performed is cleaned in a state where the extension rod is not inserted in the blow nozzle.

Further, in the aseptic filling method according to the present invention, preferably, the interior of the chamber in which the molding and filling step is performed is sterilized with a gas or mist of hydrogen peroxide or a mixture thereof in a state where a temperature of an outer surface of the blow nozzle is equal to or higher than 60° C. as a result of a flow path in the blow nozzle being cleaned or sterilized.

Further, in the aseptic filling method according to the present invention, preferably, an inner surface of the mold is cleaned in a state where the mold is open while the mold is being rotated at a speed equal to or lower than 60 rpm.

Advantageous Effects of Invention

With the aseptic filling machine according to the present invention, a sterilized content is introduced into a sterilized preform under high pressure while maintaining the aseptic condition of the sterilized preform, and therefore, the preform can be molded into a bottle and at the same time filled with the content. The aseptic filling machine according to the present invention is substantially smaller than conventional machines and therefore requires a smaller installation space. Therefore, the initial investment cost can be reduced. According to the aseptic filling method according to the present invention, molding and filling are performed at the same time, and therefore, the process is simplified compared with conventional methods, and the running cost can be reduced. In addition, a product that is highly reliable in terms of aseptic condition can be manufactured.

DESCRIPTION OF EMBODIMENTS

Figure 1:
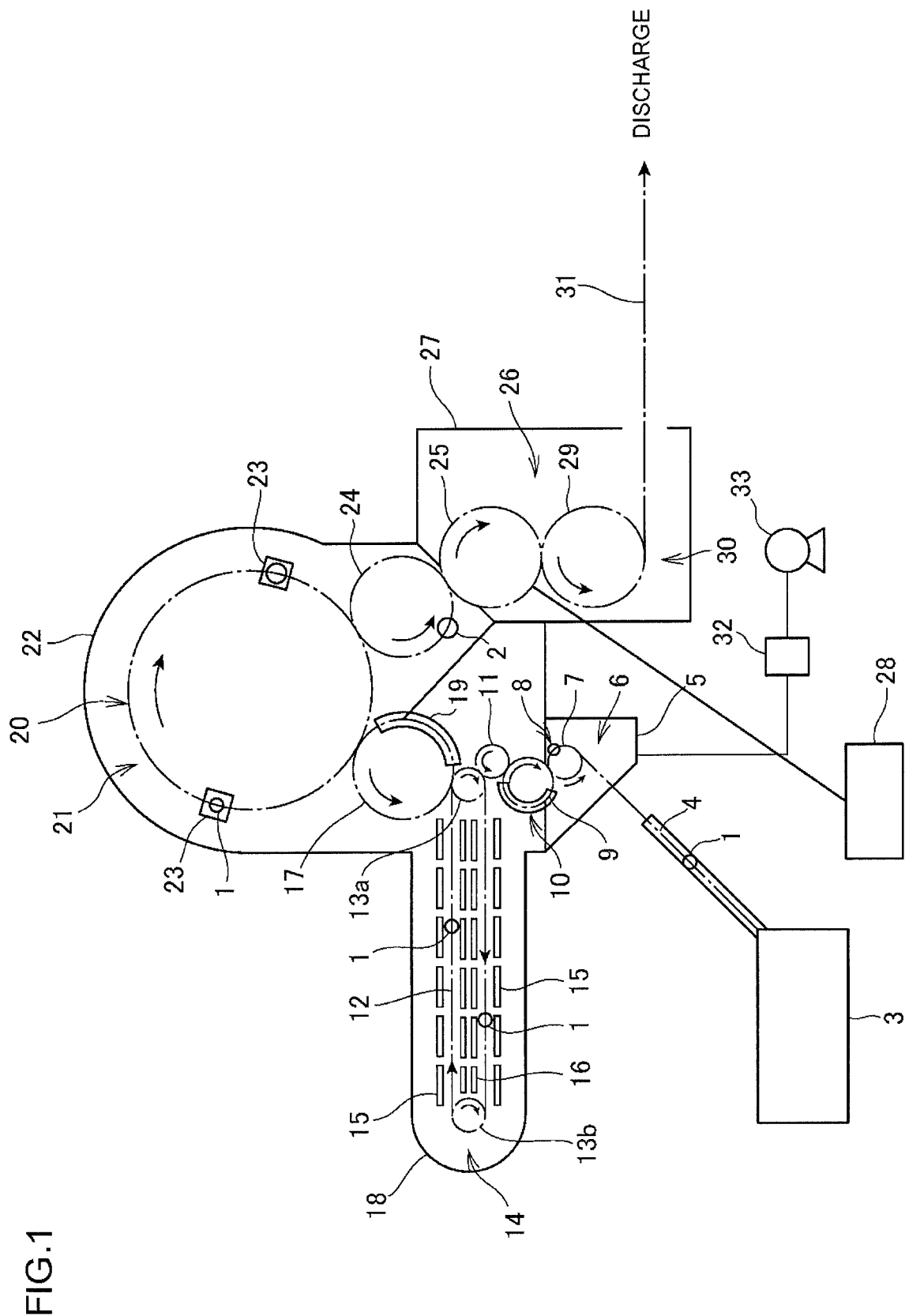
FIG. 1 is a plan view schematically showing an example of an aseptic filling machine according to a first embodiment of the present invention.

A first embodiment of the present invention of this application will be described below with reference to the drawings.

First Embodiment

An aseptic filling machine will be first schematically described with reference to FIG. 1, and then the aseptic filling machine and an aseptic filling method therefor will also be described in detail with reference to other drawings. The aseptic filling machine includes a pre-heating sterilizing portion 6 that sterilizes a preform 1 supplied from a preform supplying apparatus 3, a heating portion 14 that heats the sterilized preform 1 to a temperature for molding the preform 1 into a bottle 2, a molding and filling portion 21 that molds the heated preform 1 into the bottle 2 and at the same time fills the bottle 2 with a content, and a sealing portion 26 that seals the bottle 2 filled with the content. According to the first embodiment, the sterilized preform 1 can be filled with the content while being molded, and an aseptic product filled with a content can be produced with a reduced number of steps compared with prior art.

(Outline of Aseptic Filling Machine According to First Embodiment)

As shown in FIG. 1, the aseptic filling machine according to the first embodiment includes the preform supplying apparatus 3 that supplies the preform 1, the pre-heating sterilizing portion 6 that sterilizes the preform, the heating portion 14 that heats the preform 1 to a temperature for molding the preform 1 into the bottle 2, the molding and filling portion 21 that molds the heated preform 1 into the bottle 2 and at the same time fills the bottle 2 with a sterilized content, and the sealing portion 26 that seals the bottle 2 filled with the content with a sterilized cap 35. The aseptic filling machine further includes a discharging portion 30 in which the sealed bottle 2 is placed on a discharging conveyor 31 and discharged to a non-aseptic zone.

The sterilizing portion 6 is shielded by a pre-heating sterilizing portion chamber 5, the heating portion 14 is shielded by a heating portion chamber 18, the molding and filling portion 21 is shielded by a molding and filling portion chamber 22, and the sealing portion 26 and the discharging portion 30 are shielded by a sealing portion chamber 27. The molding and filling portion 21 and the sealing portion 26 may be shielded by a single chamber. Depending on a preform sterilizing device in the pre-heating sterilizing portion 6, a gas or mist of a sterilizer, a mixture thereof, or ozone can be produced in the pre-heating sterilizing portion chamber 5. To prevent these from flowing into the heating portion 14, the gas in the pre-heating sterilizing portion 6 is discharged by an exhaust gas blower 33 through an exhaust gas processing apparatus 32 that detoxifies the gas or mist of the sterilizer, a mixture thereof, or ozone.

Of the pre-heating sterilizing portion chamber 5, the heating portion chamber 18, the molding and filling portion chamber 22 and the sealing portion chamber 27, at least the molding and filling portion chamber 22 and the sealing portion chamber 27 are provided with a sterilizing apparatus, and the interior of each of the chambers is sterilized before starting operating the aseptic filling machine. The interior of the pre-heating sterilizing portion chamber 5 can be sterilized when the preform 1 is sterilized, and therefore does not need to be sterilized before the aseptic filling machine starts operating. Further, the temperature in the heating portion chamber 18 is relatively high because the heating portion heats the preform 1, and bacteria or the like is unlikely to enter the preform 1 because a spindle 52 is inserted into a mouth portion 1a of the preform 1, so that the interior of the heating portion chamber 18 does not need to be sterilized before the aseptic filling machine starts operating.

The sterilizing apparatus includes a sterilizer blasting nozzle, such as a single-fluid spray or a twin-fluid spray that mixes a sterilizer with compressed air and sprays the mixture, and a sterilizer supplying unit that supplies the sterilizer to the sterilizer blasting nozzle. The sterilizer blasting nozzle blasts the sterilizer to the entire surface of the interior of the chamber. The blasted sterilizer sterilizes the interior of the chamber. The sterilizer blasting nozzle is arranged so that the sterilizer adheres to the entire surface of the interior of the chamber. After the sterilizer is blasted, aseptic air at room temperature or heated is blasted into the chamber to active the remaining sterilizer in the chamber for removal. Before blasting of the aseptic air, aseptic water may also be blasted into the chamber to remove the sterilizer. The interior of the molding and filling portion chamber 22 and the sealing portion chamber 27 is preferably cleaned before sterilization because the content of the drink can be scattered in the chambers.

At least the molding and filling portion chamber 22 and the sealing portion chamber 27 are provided with an aseptic air supplying apparatus. After each chamber is sterilized, aseptic air, which is made aseptic by an aseptic filter, is supplied into the chamber to keep the interior of the chamber at a positive pressure. The pre-heating sterilizing portion chamber 5 and the heating portion chamber 18 may also be provided with an aseptic air supplying apparatus. By keeping the interior of each chamber at a positive pressure with the aseptic air, the aseptic condition of the aseptic filling machine is maintained. The positive pressure in the molding and filling portion chamber 22 is the highest, and the positive pressures in the heating portion chamber 18 and the sealing portion chamber 27 are set to be lower than the positive pressure in the molding and filling portion chamber. The pressure in the pre-heating sterilizing portion chamber 5 is substantially kept at atmospheric pressure, since the gas in the pre-heating sterilizing portion chamber 5 is discharged. The pre-heating sterilizing portion chamber 5 may be provided with no aseptic air supplying apparatus, and the aseptic air in the heating portion chamber 18 may be the only air that flows into the pre-heating sterilizing portion chamber 5. Each of the other chambers than the pre-heating sterilizing portion chamber 5 may also be provided with an exhaust apparatus, and the aseptic air supplying apparatus and the exhaust apparatus may cooperate to keep the interior of the chamber at an appropriate pressure. If the molding and filling portion 21 and the sealing portion 26 are shielded by a single chamber, the single chamber may be provided with one aseptic air supplying apparatus and one exhaust apparatus.

(Details of Aseptic Filling Machine and Aseptic Filling Method According to First Embodiment)

Figure 2:
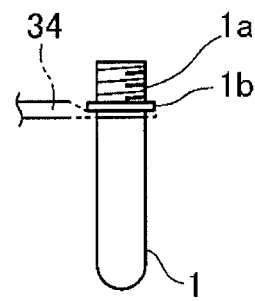
FIG. 2 a diagram for illustrating a preform supply step according to the embodiment of the present invention.

Preforms such as the preform 1 shown in FIG. 2 are successively conveyed from the preform supplying apparatus 3 shown in FIG. 1 to the pre-heating sterilizing portion 6 at a desired speed by a preform supply conveyor 4.

Figure 13:
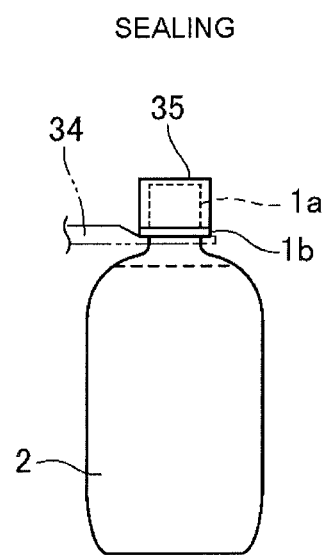
FIG. 13 is a diagram for illustrating a bottle sealing step according to the embodiment of the present invention.

The preform 1 according to the first embodiment of the present invention is a bottomed cylindrical body having a test tube shape as shown in FIG. 2. The preform 1 is formed with a mouth portion 1*a* like that of the bottle 2 shown in FIG. 13 in an early stage of the molding of the preform 1. A male thread is formed on the mouth portion 1*a* at the same time as the molding of the preform 1. Further, a support ring 1*b* used for conveyance is formed below the mouth portion 1*a* in the preform 1. The preform 1 or the bottle 2 travels in the aseptic filling machine with the support ring 1*b* gripped by a gripper 34. The preform 1 is molded by injection molding, compression molding or the like. The preform 1 is made of a thermoplastic resin, such as polyethylene terephthalate, polyethylene naphthalate, polypropylene or polyethylene, or a mixture thereof, and may contain a recycled thermoplastic resin. Further, to have a barrier property, the preform 1 may include a layer of a thermoplastic resin, such as ethylene vinyl alcohol copolymer or polyamide having metaxylylene diamine or other aromatic amine as a monomer, or may contain such a thermoplastic resin mixed with the above described material.

The preform 1 conveyed into the pre-heating sterilizing portion 6 is conveyed to a pre-heating sterilizing wheel 7 on which a large number of grippers 34 are provided at regular pitches and sterilized on the wheel 7. A pre-heating sterilization step of sterilizing the preform 1 is achieved by any one or more of contact with a sterilizer, irradiation with an electron beam, irradiation with light containing ultraviolet radiation, contact with hot water, and contact with overheated vapor. The pre-heating sterilizing wheel 7 is provided with a pre-heating sterilizing device 8 that achieves the pre-heating sterilization step. The preform 1 may be preheated by hot air before sterilization. To preheat the preform 1, a preheating wheel may be provided before the pre-heating sterilizing wheel 7. Preheating of the preform 1 improves the sterilization effect.

Figure 3:
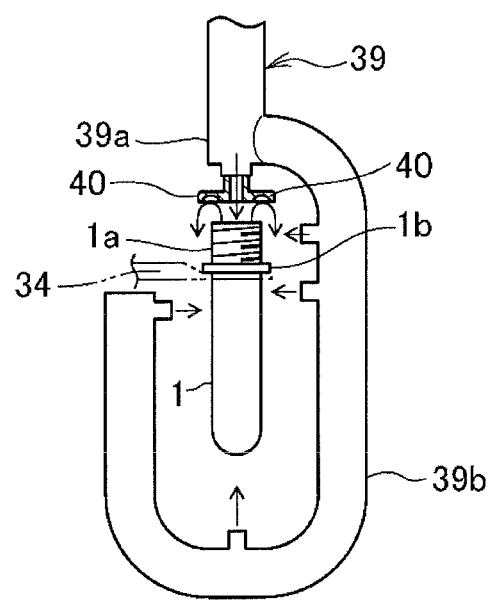
FIG. 3 is a diagram for illustrating a step of blasting a sterilizer gas to a preform according to the embodiment of the present invention.
Figure 4:
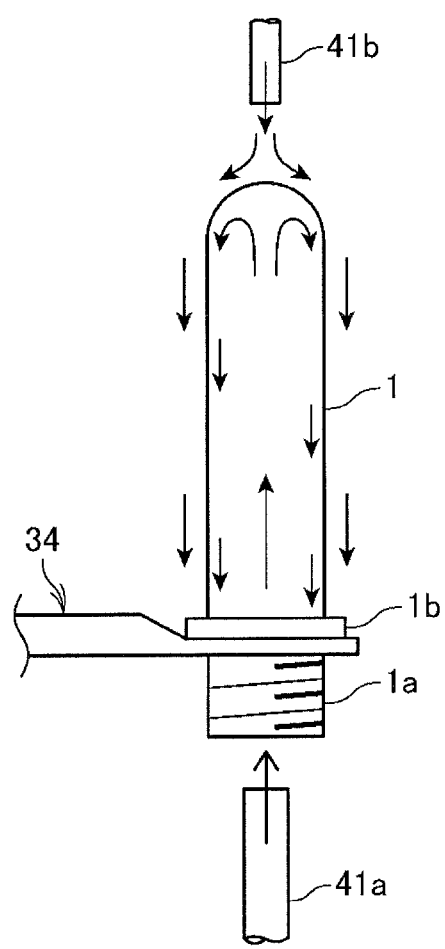
FIG. 4 is a diagram for illustrating a step of blasting a liquid sterilizer to a preform according to the embodiment of the present invention.

The contact of the preform 1 with a sterilizer according to the first embodiment of the present invention is to blast a gas or mist of a sterilizer or a mixture thereof to the preform 1 as shown in FIG. 3 or blasting a liquid sterilizer to the preform 1 inverted as shown in FIG. 4.

The sterilizer blasted to the preform 1 in the form of gas, mist or a mixture thereof preferably contains at least hydrogen peroxide. An appropriate range of the content of hydrogen peroxide is from 0.5% by mass to 65% by mass. If the content is lower than 0.5% by mass, the sterilizing power may be insufficient in some cases, while if the content is higher than 65% by mass, the sterilizer will be difficult to handle from the viewpoint of safety. A further preferable range is from 0.5% by mass to 40% by mass. When the content is equal to or lower than 40% by mass, it is easier to handle the sterilizer, and the residual amount of the sterilizer after sterilization can be reduced since the concentration of hydrogen peroxide is low. The sterilizer contains water. However, the sterilizer may contain one or more of alcohols such as methyl alcohol, ethyl alcohol, isopropyl alcohol, n-propyl alcohol and butyl alcohol, ketones such as acetone, methyl ethyl ketone and acetylacetone, and glycol ether and the like. The sterilizer may further contain an additive agent such as a compound having a sterilizing effect such as an organic acid including peracetic acid or acetic acid, an inorganic acid including nitric acid, a basic compound including sodium hydroxide or potassium hydroxide, sodium hypochlorite, chlorine dioxide or ozone, a cationic surface active agent, a non-ionic surface active agent, or a phosphate compound.

Figure 5:
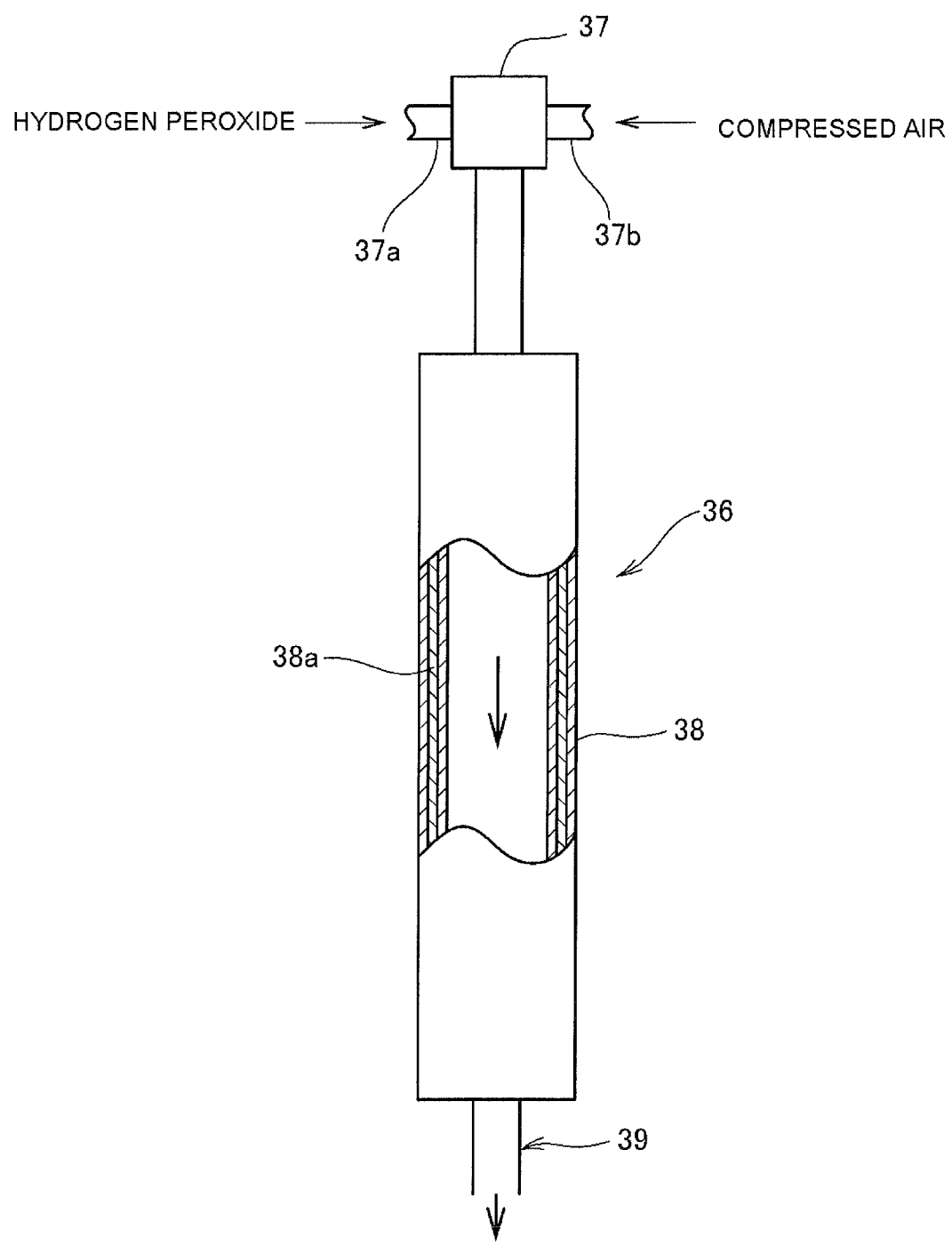
FIG. 5 shows a sterilizer gas generator according to the embodiment of the present invention.

The gas or mist of the sterilizer or a mixture thereof blasted to the preform 1 is generated by a sterilizer gas generator 36 shown in FIG. 5. The sterilizer gas generator 36 includes a sterilizer supply portion 37 that is a twin-fluid spray nozzle that supplies a sterilizer in the form of drops, and a vaporizing portion 38 that vaporizes the sterilizer supplied from the sterilizer supply portion 37 by heating the sterilizer to a temperature equal to or lower than the decomposition temperature thereof. The sterilizer supply portion 37 is configured to receive the sterilizer and compressed air that are introduced from a sterilizer supply path 37*a* and a compressed air supply path 37*b*, respectively, and to spray the sterilizer into the vaporizing portion 38. The vaporizing portion 38 is a pipe that incorporates a heater 38*a* disposed between inner and outer walls thereof, and heats and vaporizes the sterilizer blasted into the pipe. The gas of the vaporized sterilizer is ejected to the outside of the vaporizing portion 38 from a sterilizer gas blasting nozzle 39. The vaporizing portion 38 may be heated by dielectric heating or overheated steam instead of the heater 38*a*.

As the operating condition of the sterilizer supply portion 37, for example, the pressure of the compressed air is adjusted within the range of 0.05 MPa to 0.6 MPa. The amount of the supplied compressed air is appropriately from 50 L/min to 300 L/min. The sterilizer may be supplied by gravity or pressure, and the amount of the supplied sterilizer can be arbitrarily set. For example, the sterilizer is supplied in an amount within a range of 1 g/min to 100 g/min. Furthermore, the sprayed sterilizer is vaporized by heating the inner surface of the vaporizing portion 38 to a temperature from 120° C. to 450° C.

The gas of the sterilizer is blasted from the sterilizer gas blasting nozzle 39 to the preform 1 as shown in FIG. 3. The gas of the sterilizer is divided into two streams in the sterilizer gas blasting nozzle 39, one of the streams is blasted into the preform 1 from one nozzle part 39*a*, and the other stream is blasted to the outer surface of the preform 1 from a nozzle part 39*b*. After exiting from the sterilizer gas blasting nozzle 39, the gas of the sterilizer flows into the preform 1 or comes into contact with the outer surface of the preform 1 in the form of gas, mist or a mixture thereof.

The gas or mist of the sterilizer or a mixture thereof blasted into the preform 1 flows into the preform 1 and then overflows from the mouth portion 1*a* of the preform 1. The flow of the gas or the like of the sterilizer overflowing collides against an umbrella-shaped member 40 and is guided by the inner surface of the umbrella-shaped member 40 to change direction toward the outer surface of the preform 1 and come into contact with the outer surface of the preform 1. If an annular groove 40*a* is formed in the umbrella-shaped member 40, the gas or the like of the sterilizer overflowing flows along the outer surface of the preform 1.

Although the blasting amount of the gas or mist of the sterilizer or a mixture thereof is arbitrarily set, the blasting amount is determined by the amount of the sterilizer supplied to the sterilizer gas generator 36 and the duration of blasting. A plurality of sterilizer gas generators 36 may be provided. The blasting amount also depends on the size of the preform 1. The gas or mist of the sterilizer or a mixture thereof ejected from the sterilizer gas blasting nozzle 39 may be diluted with hot air before being blasted to the preform 1.

When a hydrogen peroxide solution is used as the sterilizer, the blasting amount of the gas of the hydrogen peroxide solution is as follows. The amount of the hydrogen peroxide adhering to the preform 1 that derives from the gas or the like of the hydrogen peroxide solution blasted to the preform 1 from the sterilizer gas blasting nozzle 39 is preferably within a range of 0.0035 $\mu L/cm^2$ to 0.35 $\mu L/cm^2$ when the hydrogen peroxide solution contains 35% by mass of hydrogen peroxide. The hydrogen peroxide concentration of the gas or the like of the hydrogen peroxide solution blasted to the preform 1 is preferably within a range of 2 mg/L to 20 mg/L, and more preferably is within a range of 5 mg/L to 10 mg/L.

Once the gas or mist of the sterilizer or a mixture thereof is blasted to the preform 1, the preform 1 is preferably rinsed with aseptic air. A nozzle for blasting the air to the preform 1 may be arranged to be opposed to the mouth portion 1*a* of the preform 1, or a nozzle moving at the same speed as the preform 1 being conveyed may be inserted into the preform 1. Such aseptic air rinsing has effects of activating the sterilizer blasted on the preform 1 and removing the sterilizer remaining on the inner surface of the preform 1 and foreign matters or dust on the inner surface. The air used for the aseptic air rinsing may be at room temperature or may be heated. The heated air is more effective for activating the sterilizer. The aseptic air rinsing may be performed with the preform 1 standing in the upright or inverted position. The inverted position is more preferable from the viewpoint of removing foreign matters. Further, from the viewpoint of removing foreign matters, the air in the inverted preform 1 is preferably sucked through the mouth portion 1*a* of the preform 1. The amount of the air blasted is preferably from 0.04 L/preform to 400 L/preform. When the sterilizer is a hydrogen peroxide solution, the amount of the hydrogen peroxide adhering to the preform 1 after the aseptic air rinsing is preferably from 0.0003 $\mu L/cm^2$ to 0.35 $\mu L/cm^2$ in terms of concentration of a hydrogen peroxide solution containing 35% by mass of hydrogen peroxide. A more preferable range is 0.0004 $\mu L/cm^2$ to 0.2 $\mu L/cm^2$. When the adhering amount of hydrogen peroxide is equal to or higher than 0.0003 $\mu L/cm^2$, an adequate sterilization effect can be achieved. If the adhering amount of hydrogen peroxide is higher than 0.35 $\mu L/cm^2$, the amount of the hydrogen peroxide remaining on the bottle 2 increases.

In the sterilization method that involves blasting a gas or mist of a sterilizer or a mixture thereof to the preform 1, such a gas or mist of a sterilizer or a mixture thereof is produced in the blasting step and the subsequent air rinsing step, the gas in the pre-heating sterilizing portion chamber 5 needs to be discharged. The discharged gas is detoxified by the exhaust gas processing apparatus 32 and released by the exhaust gas blower 33.

A liquid sterilizer is blasted to the inverted preform 1 as shown in FIG. 4. In order that the liquid sterilizer comes into contact with the entire inner surface of the preform 1, the support ring 1*b* of the inverted preform 1 is gripped by the gripper 34, and the liquid sterilizer is blasted from a sterilizer blasting nozzle 41*a* facing upward to the inner surface of the preform 1 through the mouth portion 1*a*. In order that the liquid sterilizer comes into contact with the entire outer surface of the preform 1, the liquid sterilizer is blasted from a sterilizer blasting nozzle 41*b* facing downward to the outer surface of the preform 1. The sterilizer blasting nozzle 41*a* may be arranged to be opposed to the mouth portion 1*a* of the preform 1 or may be arranged to move at the same speed as the preform 1 being conveyed and inserted into the preform 1. A plurality of sterilizer blasting nozzles 41*b* may be provided. Since it is essential only that the liquid sterilizer comes into contact with the inner and outer surfaces of the preform 1, the preform 1 may be immersed in the liquid sterilizer, instead of using the nozzles to blast the liquid sterilizer.

The liquid sterilizer preferably contains peracetic acid. The liquid sterilizer is more preferably a balanced peroxide composition composed of peracetic acid, hydrogen peroxide, acetic acid and water. The concentration of peracetic acid is preferably from 500 mg/L to 4000 mg/L. If the concentration is lower than 500 mg/L, the sterilization power is inadequate, while if the concentration is higher than 4000 mg/L, the excessively high concentration of peracetic acid can cause deterioration of packings or other members in the aseptic filling machine. Alternatively, a sterilizer containing a sterilizing constituent such as hydrogen peroxide, sodium hypochlorite, chlorine dioxide or ozone may be used as the liquid sterilizer. The liquid sterilizer contains water. However, the liquid sterilizer may contain one or more of alcohols such as methyl alcohol, ethyl alcohol, isopropyl alcohol, n-propyl alcohol and butyl alcohol, ketones such as acetone, methyl ethyl ketone and acetylacetone, and glycol ether and the like. The liquid sterilizer may further contain an additive agent such as an inorganic acid including nitric acid, a basic compound including sodium hydroxide or potassium hydroxide, a cationic surface active agent, a non-ionic surface active agent or a phosphate compound.

Although the liquid sterilizer may be at room temperature, the liquid sterilizer is preferably heated to 40° C. to 80° C. The heated sterilizer has an improved sterilization effect. The flowrate of each of the sterilizer blasting nozzles 41*a* and 41*b* is from 1 L/min to 15 L/min, and is preferably from 3 L/min to 10 L/min. The duration of blasting is appropriately from 0.2 seconds to 5 seconds. The amount of the liquid sterilizer blasted to the preform 1 is determined by the flowrate of the sterilizer blasting nozzles 41*a* and 41*b* and the duration of blasting, and is preferably from 0.05 ml/cm$^2$ to 20 ml/cm$^2$ with respect to the surface area of the preform 1. If the amount is lower than 0.05 ml/cm$^2$, the sterilization power is inadequate, while if the amount is higher than 20 ml/cm$^2$, the amount is excessive, leading to waste of energy and sterilizer.

The preform 1 having come into contact with the liquid sterilizer is rinsed with aseptic water to remove the adhering sterilizer. The aseptic water is produced by heating water to a temperature equal to or higher than 121° C. for four or more minutes, or passing water through an aseptic filter. The aseptic water may be water processed under sterilization conditions equivalent to or stricter than those for the content to fill the preform 1. For example, if the content to fill the preform 1 is mineral water, the preform 1 may be rinsed with the mineral water that is to fill the preform 1. The rinsing of the preform 1 with aseptic water is performed in a manner similar to the manner of blasting the sterilizer shown in FIG. 4 by an apparatus similar to that used for the blasting of the sterilizer shown in FIG. 4. In order that the entire inner surface of the preform 1 is rinsed with the aseptic water, the support ring 1b of the inverted preform 1 is gripped by the gripper 34, and the aseptic water is blasted from a nozzle facing upward to the inner surface of the preform 1 through the mouth portion 1a. In order that the entire outer surface of the preform 1 is rinsed with the aseptic water, the aseptic water is blasted from a nozzle facing downward to the outer surface of the preform 1. The nozzle facing upward may be arranged to be opposed to the mouth portion 1a of the preform 1 or may be arranged to move at the same speed as the preform 1 being conveyed and inserted into the preform 1. A plurality of nozzles facing downward may be provided.

The temperature of the aseptic water is adjusted to fall within a range of 10° C. to 80° C. or preferably a range of 30° C. to 70° C. The flowrate of the aseptic water blasted by each nozzle is from 1 L/min to 15 L/min, and preferably from 3 L/min to 10 L/min. The duration of blasting is appropriately from 0.1 seconds to 15 seconds. The amount of the aseptic water blasted to the preform 1 is determined by the flowrate of the nozzles and the duration of blasting, and is preferably from 0.05 ml/cm$^2$ to 20 ml/cm$^2$ with respect to the surface area of the preform 1. If the amount is lower than 0.05 ml/cm$^2$, the rinsing is inadequate, while if the amount is higher than 20 ml/cm$^2$, energy is wasted.

The aseptic water adhering to the preform 1 rinsed with the aseptic water is preferably removed by blasting aseptic air to the inner and outer surfaces of the preform 1. The preform 1 is heated to a molding temperature in the heating portion 14. If the aseptic water remains on apart of the preform 1, the part is unevenly heated, and molding defects such as whitening or thickness variations can occur on the molded bottle 2. The aseptic air is preferably compressed air rather than blower air, and the pressure of the aseptic air is equal to or higher than 0.01 MPa, or preferably from 0.1 MPa to 0.6 MPa. The inner diameter of the nozzle used for blasting the aseptic air is $\phi$1 mm to $\phi$10 mm, or preferably $\phi$2 mm to $\phi$8 mm. When the liquid sterilizer is a hydrogen peroxide solution, the amount of the hydrogen peroxide adhering to the preform 1 after the aseptic air rinsing is preferably from 0.0003 μL/cm$^2$ to 0.35 μL/cm$^2$ in terms of concentration of a hydrogen peroxide solution containing 35% by mass of hydrogen peroxide. A more preferable range is 0.0004 μL/cm$^2$ to 0.2 μL/cm$^2$. When the adhering amount of hydrogen peroxide is equal to or higher than 0.0003 μL/cm$^2$, an adequate sterilization effect can be achieved. If the adhering amount of hydrogen peroxide is higher than 0.35 μL/cm$^2$, the amount of the hydrogen peroxide remaining on the bottle 2 increases.

Figure 6:
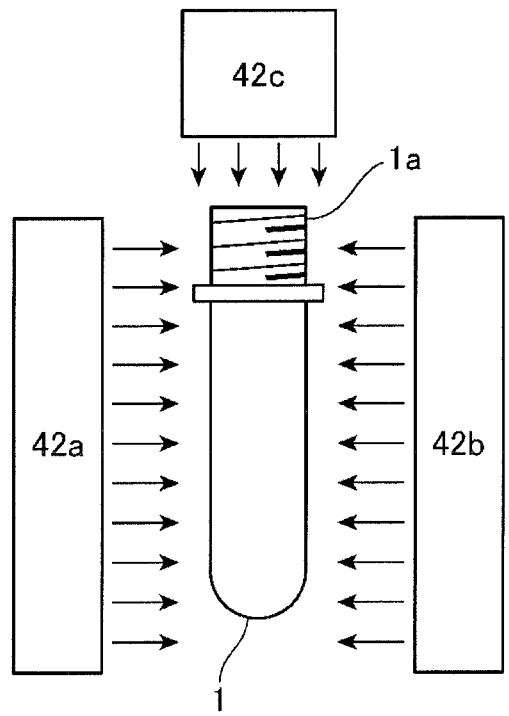
FIG. 6 is a diagram for illustrating a step of irradiating a preform with an electron beam according to the embodiment of the present invention.

The irradiation of the preform 1 with an electron beam according to the first embodiment of the present invention is to irradiate the inner and outer surfaces of the preform 1 being conveyed with an electron beam by electron beam irradiating device 42a, 42b and 42c as shown in FIG. 6. The electron beam has a sterilization effect, and bacteria or the like on the surface of the preform 1 is killed by irradiation with the electron beam. Although the preform 1 is irradiated with an electron beam from three directions in FIG. 6, the preform 1 can be irradiated with an electron beam in any manner as far as the inner and outer surfaces of the preform 1 are irradiated with an electron beam. For example, if the preform 1 is rotated, the electron beam irradiating device 42b can be omitted. Further, a reflection mirror may be arranged above the mouth portion 1a of the preform 1 so that the electron beam emitted from the electron beam irradiating device 42a can be introduced into the preform 1 through the mouth portion 1a of the preform 1. Further, a rod-shaped electron beam irradiating device may be inserted into the preform 1 to irradiate the inner surface of the preform 1 with an electron beam.

The electron beam irradiating apparatuses 42a, 42b and 42c can have any configuration. For example, the electron beam irradiating apparatuses may be of the scanning type or the monofilament type, and is preferably of the low power type of 100 kV to 500 kV because of its high operability.

Before the preform 1 is irradiated with an electron beam, foreign matters are preferably removed from the inner and outer surfaces of the preform 1. If there are foreign matters on the surface of the preform. 1, the parts of the surface under the foreign matters are not adequately irradiated with the electron beam and therefore can be poorly sterilized. Foreign matters are removed from the preform 1 by blasting air or water to the preform 1 in the upright or inverted position. When water is used, the blasted water needs to be removed. For this reason, air is preferably used. Before air is blasted, static electricity is preferably removed from the preform 1 by, for example, blasting ionized air to the preform 1. Further, a suction nozzle is preferably arranged in the vicinity of the mouth portion 1a of the preform 1 to suck and remove foreign matters to the outside of the aseptic filling machine. The step of removing foreign matters from the preform 1 is performed on the preform supply conveyor 4, which is located outside the pre-heating sterilizing portion chamber 5, and after foreign matters are removed, the preform 1 is conveyed into the pre-heating sterilizing portion chamber 5.

The electron beam turns oxygen into ozone. Therefore, if there is oxygen in the atmosphere in which the electron beam irradiation occurs, ozone is produced. To remove the ozone produced, the gas in the pre-heating sterilizing portion chamber 5 needs to be discharged. If the atmosphere in which the electron beam irradiation occurs is replaced with nitrogen or the like, production of ozone can be suppressed.

Figure 7:
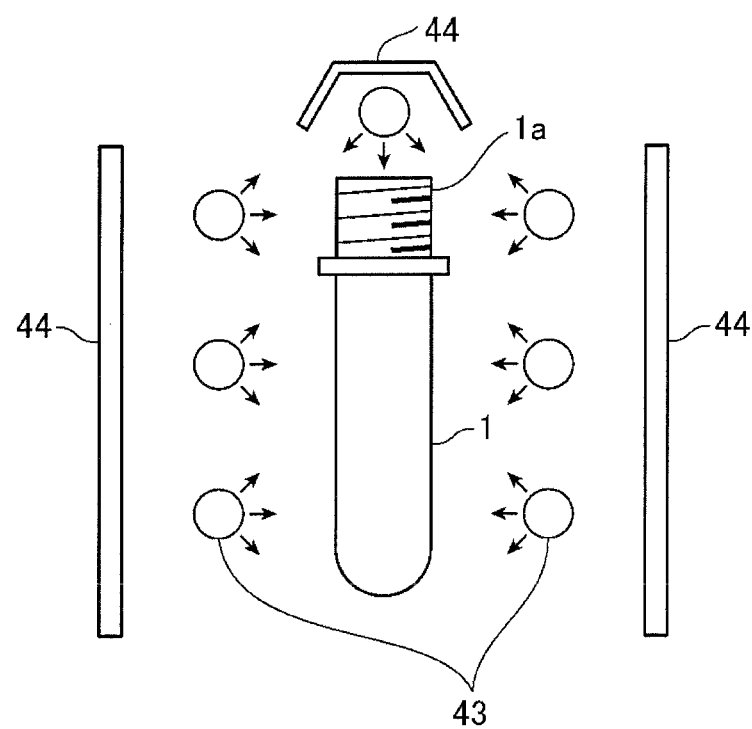
FIG. 7 is a diagram for illustrating a step of irradiating a preform with light containing ultraviolet radiation according to the embodiment of the present invention.

The irradiation of the preform 1 with light containing ultraviolet radiation according to the first embodiment of the present invention is to irradiate the inner and outer surfaces of the preform 1 with light containing ultraviolet radiation emitted from a light irradiation lamp 43 as shown in FIG. 7. On the opposite side of the preform 1 to the light irradiation lamp 43, a light reflecting plate 44 is preferably arranged to reflect the irradiation light toward the preform 1.

The ultraviolet radiation contained in the irradiation light is a kind of electromagnetic wave that has a wavelength from 100 nm to 380 nm. Although the irradiation light can have any wavelength in this range, an ultraviolet radiation having a wavelength of 100 nm to 280 nm, which is referred to as UV-C, is particularly effective for sterilization. An ultraviolet radiation having a wavelength of 253.7 nm is more effective for sterilization, and the irradiation light preferably contains this ultraviolet radiation.

The light irradiation lamp 43 that emits an ultraviolet radiation having a wavelength of 100 nm to 380 nm is a low-pressure mercury lamp, a high-pressure mercury lamp, or a xenon flash lamp, for example. In particular, light (having a wavelength of 100 to 950 nm) emitted from the xenon flash lamp in which xenon gas is sealed has a high sterilization effect, and the light irradiation lamp 43 is appropriately a xenon flash lamp.

The sterilization effect of the irradiation with the light containing ultraviolet radiation is proportional to the irradiation amount of light per unit area and the duration of irradiation. Since the light from the xenon flash lamp has higher sterilization effect than the light from the low-pressure mercury lamp or high-pressure mercury lamp, however, the preform 1 can be adequately sterilized by short-time irradiation, so that the temperature of the mouth portion of the preform 1 can be prevented from being raised by the light irradiation.

Any number of light irradiation lamps 43 can be provided, as far as the whole of the inner and outer surfaces of the preform 1 are irradiated with light. A large number of light irradiation lamps 43 may be provided as shown in FIG. 7, in order to irradiate the inner and outer surfaces of the preform 1 with the light containing ultraviolet radiation. However, if the preform 1 is rotated, a single row of light irradiation lamps 43 may suffice to irradiate the side surface of the preform 1. In order to irradiate the inner surface of the preform 1 with the light containing ultraviolet radiation, a light irradiation lamp 43 is preferably arranged to be opposed to the mouth portion 1a of the preform 1 so that the inner surface of the preform 1 is irradiated with the light containing ultraviolet radiation through the opening of the mouth portion 1a. In addition, a dome-shaped light reflecting plate 44 is preferably arranged to face the mouth portion 1a so that the inner surface of the preform 1 is efficiently irradiated with the light containing ultraviolet radiation emitted from the light irradiation lamp 43. In order to irradiate the inner surface of the preform 1 with the light containing ultraviolet radiation, a rod-shaped light irradiation lamp may be inserted into the preform 1 to irradiate the inner surface of the preform 1 with the light containing ultraviolet radiation. The light irradiation lamp 43 can have any shape, such as a ball-like shape, a rod-like shape or a U-shape.

The light reflecting plates 44 shown in FIG. 7 are intended to efficiently irradiate the preform 1 with the light containing ultraviolet radiation emitted from the light irradiation lamps 43. For this reason, the light reflecting plate 44 is arranged on the opposite side of the preform 1 to the light irradiation lamp 43. The light reflecting plate 44 can have a planar surface, a curved surface or a combination of a plurality of surfaces of various shapes. Any light reflecting plate 44 can be used as far as the light reflecting plate can reflect the light containing ultraviolet radiation. For example, the light reflecting plate may be made of a synthetic resin, a metal or glass and have its surface smoothed. In order to make the surface smoother, the surface may be coated, plated with a metal or the like, subjected to vapor deposition of a metal or a metal oxide, or processed by a combination of these techniques.

Before the preform 1 is irradiated with the light containing ultraviolet radiation, foreign matters are preferably removed from the inner and outer surfaces of the preform 1. If there are foreign matters on the surface of the preform 1, the parts of the surface under the foreign matters are not adequately irradiated with the light containing ultraviolet radiation and therefore can be poorly sterilized. Foreign matters are removed from the preform 1 by blasting air or water to the preform 1 in the upright or inverted position. When water is used, the water needs to be removed. For this reason, air is preferably used. Before air is blasted, static electricity is preferably removed from the preform 1 by, for example, blasting ionized air to the preform 1. Further, a suction nozzle is preferably arranged in the vicinity of the mouth portion 1a of the preform 1 to suck and remove foreign matters to the outside of the aseptic filling machine. The step of removing foreign matters from the preform 1 is performed on the preform supply conveyor 4, which is located outside the sterilizing portion chamber 5, and after foreign matters are removed, the preform 1 is conveyed into the pre-heating sterilizing portion chamber 5.

The light containing ultraviolet radiation turns oxygen into ozone. Therefore, if there is oxygen in the atmosphere in which the irradiation with the light containing ultraviolet radiation occurs, ozone is produced. To remove the ozone produced, the gas in the pre-heating sterilizing portion chamber 5 needs to be discharged. If the atmosphere in which the irradiation with the light containing ultraviolet radiation occurs is replaced with nitrogen or the like, production of ozone can be suppressed.

The contact of the preform 1 with hot water according to the first embodiment of the present invention is performed by blasting hot water to the inner and outer surfaces of the preform 1 from a nozzle in the same manner as the step of blasting a liquid sterilizer to the inverted preform 1 shown in FIG. 4. The heat of the hot water kills bacteria or the like on the surface of the preform 1. In order that the entire inner surface of the preform 1 is sterilized by the hot water, the support ring 1b of the inverted preform 1 is gripped by the gripper 34, and the hot water is blasted from a nozzle facing upward to the inner surface of the preform 1 through the mouth portion 1a. In order that the entire outer surface of the preform 1 is sterilized by the hot water, the hot water is blasted from a nozzle facing downward to the outer surface of the preform 1. The nozzle facing upward may be arranged to be opposed to the mouth portion 1a of the preform 1 or may be arranged to move at the same speed as the preform 1 being conveyed and inserted into the preform 1. A plurality of nozzles facing downward may be provided.

The hot water is water or aseptic water heated to 70° C. to 100° C. The flowrate of each nozzle used for blasting the hot water is from 1 L/min to 15 L/min, and is preferably from 3 L/min to 10 L/min. The inner diameter of the nozzle is from φ1 mm to φ10 mm, and is preferably from φ2 mm to φ8 mm. The duration of blasting is appropriately from 0.1 seconds to 15 seconds. The amount of the hot water blasted to the preform 1 is determined by the flowrate of the nozzle and the duration of blasting, and is preferably from 0.05 ml/cm$^2$ to 20 ml/cm$^2$ with respect to the surface area of the preform 1. If the amount is lower than 0.05 ml/cm$^2$, the sterilization is inadequate, while if the amount is higher than 20 ml/cm$^2$, the amount is excessive, leading to waste of energy.

The hot water adhering to the preform 1 sterilized by the hot water is preferably removed by blasting air to the inner and outer surfaces of the preform 1. The preform 1 is heated to a molding temperature in the heating portion 14. If the hot water remains on a part of the preform 1, the part is unevenly heated, and molding defects such as whitening or thickness variations can occur on the molded container. The air blasted to the preform 1 is preferably aseptic air produced by passing air through an aseptic filter.

Figure 8:
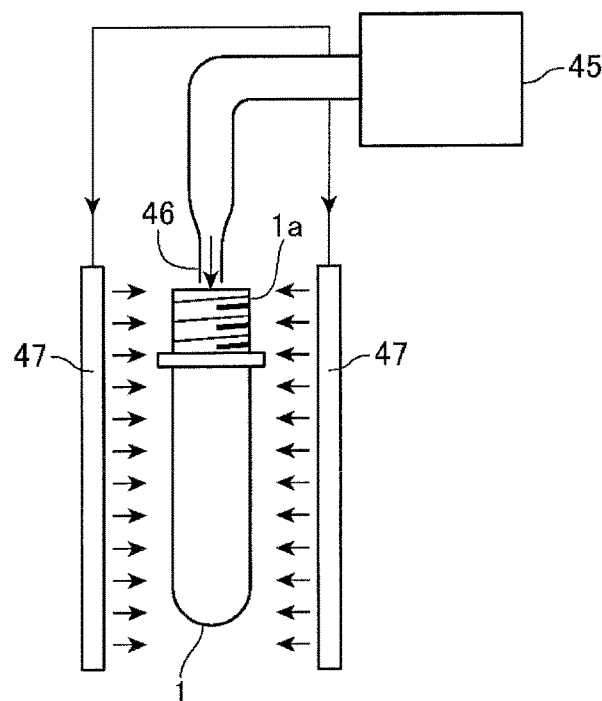
FIG. 8 is a diagram for illustrating a step of blasting overheated vapor to a preform according to the embodiment of the present invention.

The contact of the preform 1 with overheated vapor according to the first embodiment of the present invention is to blast overheated vapor generated by an overheated vapor generator 45 to the inner and outer surfaces of the preform 1 from an overheated vapor blasting nozzle 46 and an overheated vapor blasting slit 47 as shown in FIG. 8. The heat of the overheated vapor kills bacteria or the like on the surface of the preform 1.

The overheated vapor is a vapor having a temperature of 200° C. to 500° C. and a pressure of 0.1 MPa to 0.3 MPa, which is higher than atmospheric pressure, generated by the overheated vapor generator 45 from water supplied to the overheated vapor generator 45. The overheated vapor generator 45 generates the overheated vapor by a heater or induction coil heating a water pipe. The generated overheated vapor is ejected from the overheated vapor blasting nozzle 46 and blasted to the inner surface of the preform 1. The overheated vapor generated by the overheated vapor generator 45 is also introduced to the overheated vapor blasting slit 47 and blasted therefrom to the outer surface of the preform 1.

A compound having a sterilization effect, such as hydrogen peroxide, may be added to the water supplied to the overheated vapor generator 45. For example, if hydrogen peroxide is added to provide a hydrogen peroxide solution containing 1% by mass to 5% by mass of hydrogen peroxide, the sterilization effect is improved.

If the preform 1 is rotated, the overheated vapor is efficiently blasted to the outer surface of the preform 1. Further, the overheated vapor blasting nozzle 46 may be inserted into the preform 1 to blast the overheated vapor to the inner surface of the preform 1. Since the sterilization is completed by short-time blasting, deformation of the mouth portion 1a and excessive heating of the resin forming the preform 1 are avoided. Further, since no vapor drain remains in the preform 1, the preform 1 can be conveyed to the heating portion 14 without drain removal. After blasting of the overheated vapor, aseptic air may be blasted to remove foreign matters and cool the preform.

As described above, in the pre-heating sterilizing portion 6, the preform 1 is sterilized by the pre-heating sterilizing device 8 provided on the pre-heating sterilizing wheel 7 in one or more processes selected from among contact with a sterilizer, irradiation with an electron beam, irradiation with light containing ultraviolet radiation, contact with hot water, and contact with overheated vapor. The pre-heating sterilizing device 8 is provided around the pre-heating sterilizing wheel 7. However, one or more wheels may be provided in addition to the pre-heating sterilizing wheel 7, and a plurality of wheels may be provided with the pre-heating sterilizing device. Sterilization may be performed not only on the pre-heating sterilizing wheel 7 but also in the preform supplying apparatus 3 or on the preform supply conveyor 4.

Before the aseptic filling machine starts operating, the interior of the pre-heating sterilizing portion chamber 5 may be sterilized by spraying a sterilizer such as a hydrogen peroxide solution in the sterilizing portion chamber 5, for example. To this end, a sterilizer blasting nozzle is provided in the inner wall of the pre-heating sterilizing portion chamber 5. A similar sterilizer blasting nozzle is provided to sterilize the surface of the aseptic filter of the aseptic air supplying apparatus, which is adjacent to the pre-heating sterilizing portion chamber 5, that is closer to the pre-heating sterilizing portion chamber 5.

Figure 9:
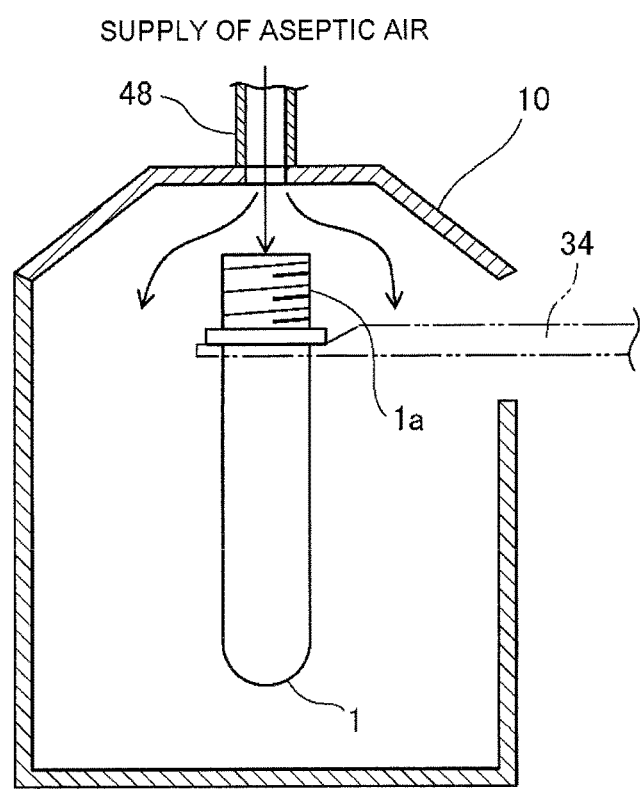
FIG. 9 is a diagram for illustrating a step of supplying aseptic air to a preform according to the embodiment of the present invention.

The preform 1 sterilized in the pre-heating sterilizing portion 6 is conveyed, with the support ring 1b thereof gripped by the gripper 34, to the heating portion conveying wheel 11 via a wheel 9. As shown in FIG. 9, a preform tunnel 10 that surrounds the conveyance path of the preform 1 may be provided for the preform 1 on the wheel 9 and the heating portion conveying wheel 11. The preform tunnel 10 covers the mouth portion 1a of the preform 1 from above, and has a ceiling portion that has a roof-like shape having an inclined surface. Further, a preform aseptic air supply nozzle 48 used for blasting aseptic air to the mouth portion 1a of the preform 1, which is formed by a row of pipes or a slit, is formed in the ceiling portion. Therefore, the aseptic air is efficiently supplied to the preform 1, and the preform 1 can travel in the heating portion chamber 18 with the aseptic condition thereof maintained. The aseptic air is produced by passing air from a blower through an aseptic filter. Alternatively, the aseptic air may be compressed air having high propulsion sterilized through an aseptic filter. The preform 1 is introduced to a heating apparatus 49 via the heating portion conveying wheel 11.

Figure 10:
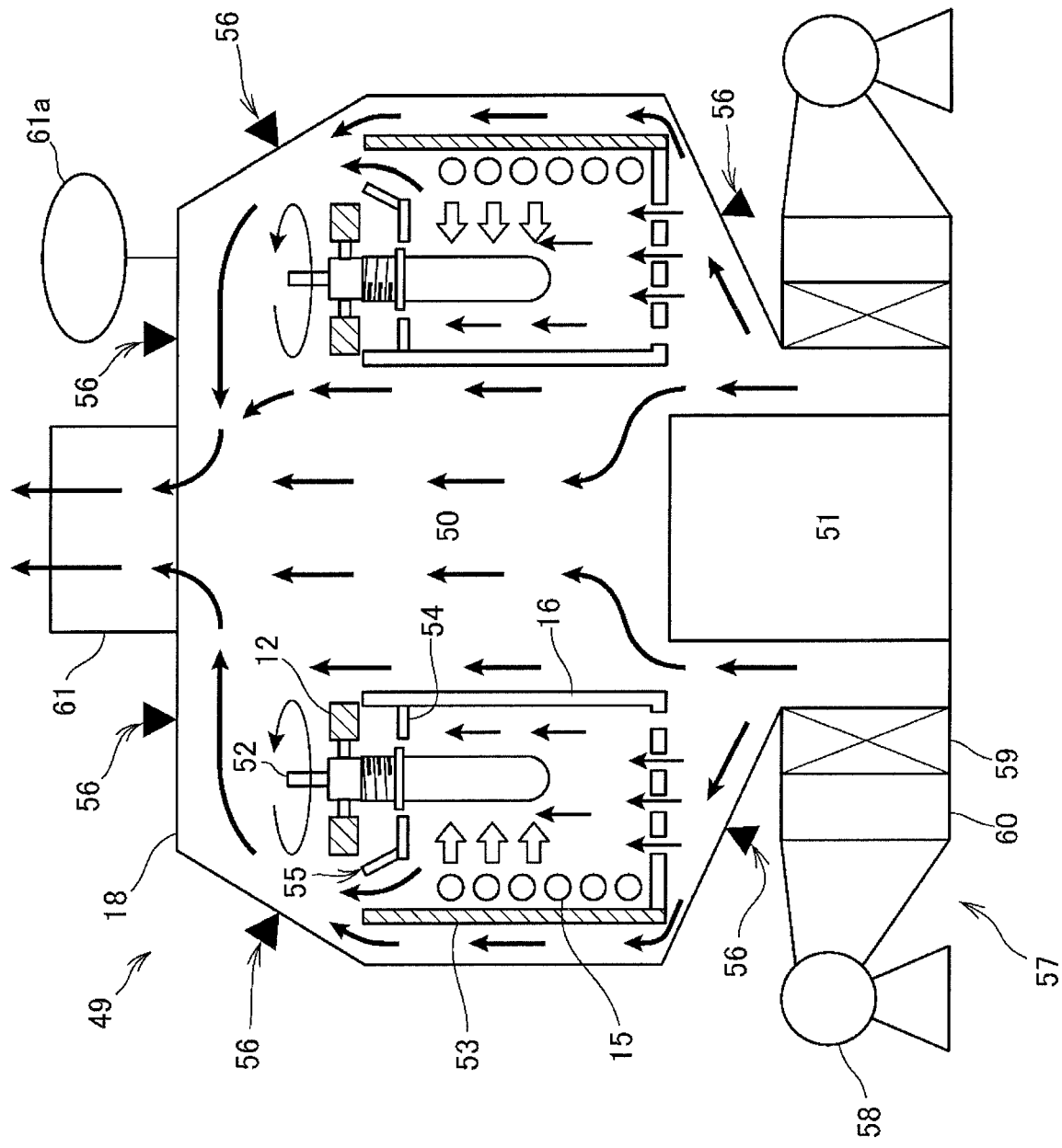
FIG. 10 is a cross-sectional view of a heating portion for a preform according to the embodiment of the present invention.

The heating apparatus 49 for the preform includes a heating furnace 50 and a driving portion 51, as shown in FIG. 10. The heating furnace 50 includes at least a heater 15 that heats the preform 1, a reflector 16 that reflects the heat of the heater 15 to efficiently heat the preform 1, a spindle 52 that holds and rotates the preform 1, an endless chain 12 for moving the spindle 52 on which spindles 52 are arranged at regular intervals, and pulleys 13a and 13b for rotating the endless chain 12. To prevent the heat of the heater 15 from being transmitted to the outside of the heating furnace 50 for the preform, a heat insulator 53 may be provided on the outer side of the heater 15.

The driving portion 51 includes a motor and a motion transmitting device, for example. The components of the driving portion 51 require lubricant and get dirty over time, and therefore it is difficult to keep the aseptic condition of the components.

The heater 15 is preferably a halogen lamp that emits infrared radiation. As the heater 15, a plurality of halogen lamps is provided in an orientation perpendicular to the axial direction of the preform 1 in parallel with each other in the vertical direction. The preform 1 is heated by the near infrared radiation, infrared radiation or far infrared radiation emitted from the halogen lamps of the heater 15. The heating temperature of the plurality of halogen lamps is controlled, and the heating temperature may vary in the axial direction of the preform 1. In the direction of travel of the preform 1, a plurality of halogen lamp units is provided as shown in FIG. 1. Although FIG. 1 shows a total of 12 units, six on each side, the number of units can be arbitrarily determined. The temperature of the halogen lamp units is controlled, and the temperature may be higher in an early stage of heating and be lower in a final stage of heating.

As shown in FIG. 10, the preform 1 having been conveyed into the heating furnace 50 is heated to a temperature suitable for the subsequent blow molding by infrared radiation heating or otherwise heating by the heater 15. The temperature is preferably 90° C. to 130° C. The temperature of the mouth portion 1a of the preform 1 is kept to be equal to or lower than 70° C., in order to prevent deformation or the like of the mouth portion 1a.

To prevent overheating of the mouth portion 1a of the preform 1, as shown in FIG. 10, a mouth protecting member 54 formed to have a surface perpendicular to the axial direction of the preform 1 is provided below the support ring 1b of the preform 1. The mouth protecting member 54 prevents more infrared radiation or the like emitted from the heater 15 than necessary from reaching the mouth portion 1a of the preform 1. In addition, to prevent the temperature of the mouth portion 1a from rising because of the ascending current caused by the heat of the heater 15, a planar heat insulating plate 55 that is inclined 90° or less with respect to the axial direction of the preform 1 may also be provided.

However, if the temperature of the mouth portion 1a is lower than 40° C., the effect of sterilization of the mouth portion 1a may deteriorate. To avoid this, the heating portion 14 may be provided with a focus lamp that actively raises the temperature of the mouth portion 1a, and the focus lamp may heat the mouth portion 1a to a temperature from 40 to 70° C. In that case, the effect of sterilization of the mouth portion 1a can be improved, and the sterilizer adhering to the surface of the mouth portion 1a can be volatilized and removed.

Although the preform 1 is heated by the infrared radiation or the like emitted from the heater 15, any infrared radiation or the like that is not absorbed by the preform 1 and goes beyond the preform 1 does not contribute to heating. In view of this, as shown in FIG. 10, if a reflector 16 is provided behind the preform 1, any infrared radiation or the like going beyond the preform 1 can be reflected to efficiently heat the preform 1. The reflector 16 is made of a metal and coated with gold, silver, aluminum or the like by vapor deposition or plating. Any reflector can be used as far as the reflector can reflect the infrared radiation or the like. The reflector 16 may have a planer surface, a curved surface or a combination thereof. In addition to the reflector 16 provided behind the preform 1, another reflector 16 may be provided behind the heater 15 so that the infrared radiation or the like emitted to the rear of the heater 15 can be reflected.

As shown in FIG. 10, the preform 1 is conveyed in the heating furnace 50 while being rotated with the spindle 52 inserted in the mouth portion 1a. When a lower part of the spindle 52 is inserted into the mouth portion 1a, an elastic body such as rubber or spring is elastically deformed to hold the preform 1 on the spindle 52. The spindle 52 is held on the endless chain 12. The endless chain 12 rotates on the pulleys 13a and 13b. Instead of the spindle 52, a mandrel may be inserted into the preform 1 to rotate and convey the preform 1 in the inverted position.

The interior of the heating portion chamber 18 may be sterilized before the heating apparatus 49 for the preform starts operating. To this end, the heating portion chamber 18 is provided with a sterilizing apparatus. The sterilizing apparatus includes at least a blasting nozzle 56 that blasts a gas or mist of a sterilizer or a mixture thereof into the heating portion chamber 18, and a sterilizer gas generator 36 that generates a sterilizer gas.

As shown in FIG. 10, the blasting nozzle 56 is provided in a wall of the heating portion chamber 18, and a gas or mist of a sterilizer or a mixture thereof is blasted from the blasting nozzle 56 into the heating portion chamber 18. From the blasting nozzle 56, the gas of the sterilizer generated by the sterilizer gas generator 36 such as one shown in FIG. 5 is blasted to the heating furnace 50 in the heating portion chamber 18, the wheel 9, the heating furnace conveying wheel 11, a wheel 17, and the wall of the heating portion chamber 18.

After the gas or mist of the sterilizer or a mixture thereof is blasted from the blasting nozzle 56 into the heating portion chamber 18, aseptic air is blasted into the heating portion chamber 18. The aseptic air vaporizes and removes any sterilizer remaining in the heating portion chamber 18. In this process, the vaporized sterilizer may also have a sterilization effect.

To blast the aseptic air into the heating portion chamber 18 from below, as shown in FIG. 10, an aseptic air supplying apparatus 57 is provided in a lower part of the heating portion chamber 18. The aseptic air supplying apparatus 57 includes a blower 58 and an aseptic filter 59. The aseptic air may be heated, and an aseptic air heating apparatus 60 is preferably provided between the blower 58 and the aseptic filter 59.

Air from the blower 58 is heated by the aseptic air heating apparatus 60 and sterilized by the aseptic filter 59, and the resulting aseptic hot air is blasted into the heating portion chamber 18 from below. Although the aseptic air may not be heated, the heated aseptic air removes the sterilizer in a shorter time and improves the sterilization effect of the sterilizer. In order to maintain the aseptic condition in the heating portion chamber 18 during operation of the heating apparatus 49 for the preform, if aseptic air is supplied into the heating portion chamber 18, the aseptic air may not be heated.

The inner surface of the aseptic filter 59, which is an HEPA filter or the like, is also sterilized by the gas or mist of the sterilizer or a mixture thereof blasted from the blasting nozzle 56 in the sterilization of the interior of the heating portion chamber 18 before the heating apparatus 49 for the preform starts operating.

Since the interior of the heating portion chamber 18 is heated by the heater 15, an ascending current occurs. If the aseptic air flows in the same direction as the ascending current, the aseptic air can smoothly flow without causing a turbulence in the heating portion chamber 18 compared with when the aseptic air flows from top to bottom. Therefore, the aseptic air is blown upward from the lower part of the heating portion chamber 18. As shown in FIG. 10, the aseptic air blown at the lower part of the heating portion chamber 18 flows upward on the inner and outer sides of the heater 15 and the reflector 16.

To efficiently heat the preform 1, the flowrate of the aseptic air flowing between the heater 15 and the reflector 16 may be controlled by adjusting the area of an opening in a plate provided below the preform 1. Further, the cooling effect of the flow of the aseptic air between the heater 15 and the reflector 16 can be reduced by heating the aseptic air.

As shown in FIG. 10, an exhaust apparatus 61 is provided on top of the heating portion chamber 18, and the aseptic air is discharged to the outside of the heating apparatus 49 for the preform, thereby keeping an appropriate pressure in the heating portion chamber 18. As shown in FIG. 10, a pressure sensor 61a is provided on top of the heating portion chamber 18 and constantly measures the pressure in the heating portion chamber 18. Based on the pressure measurement, the blower 58 and the exhaust apparatus 61 are controlled to keep an appropriate pressure in the heating portion chamber 18.

The heated preform 1 is released from the spindle 52, gripped by the gripper 34, and conveyed to a molding and filling wheel 20 in the molding and filling portion 21 via the wheel 17. On the wheel 17, as with the wheel 9, a preform tunnel 19 that surrounds the conveyance path of the preform 1 such as one shown in FIG. 9 may be provided, and aseptic air may be blasted to the preform 1.

Figure 11:
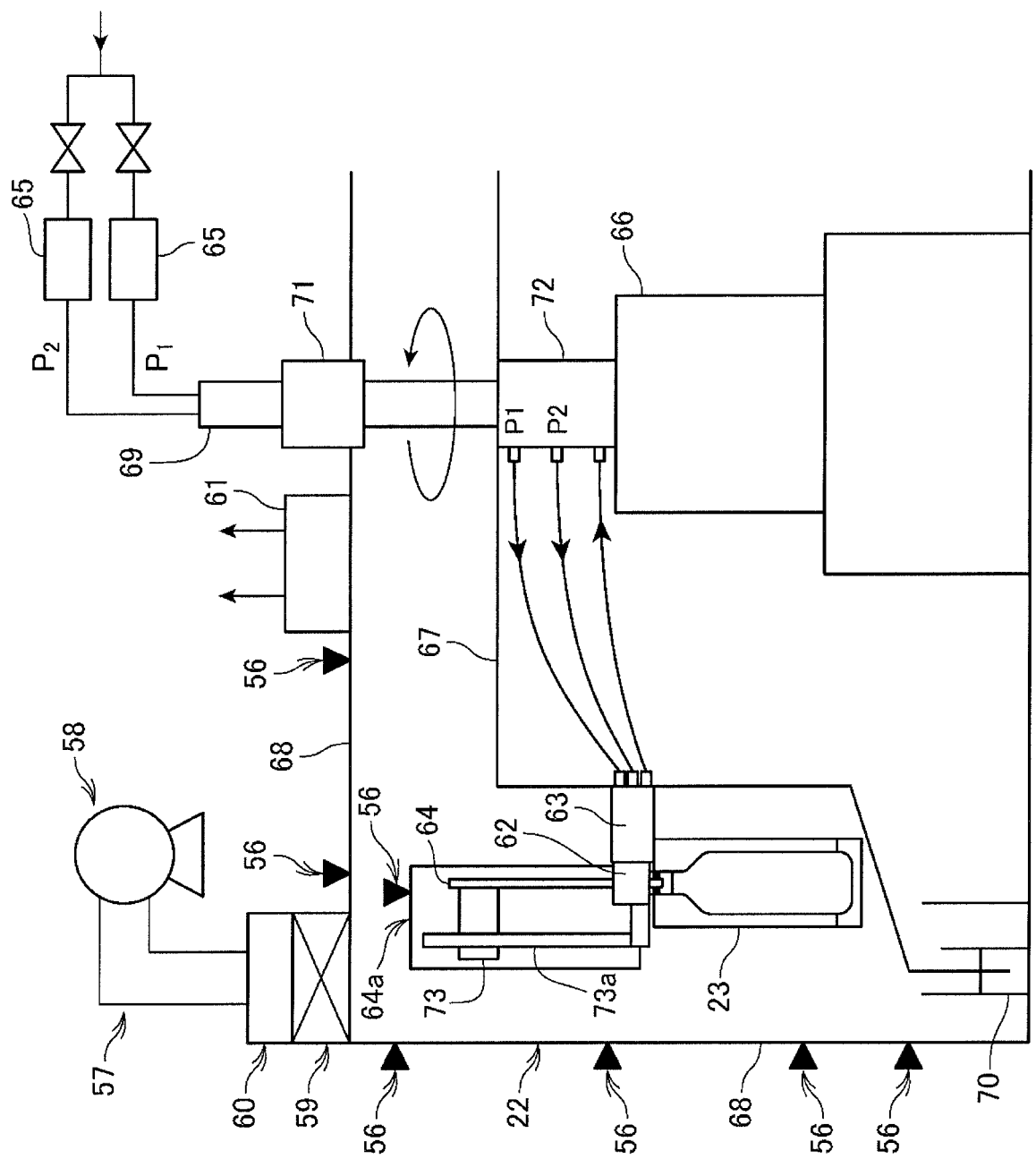
FIG. 11 is a cross-sectional view of a preform molding and filling portion according to the embodiment of the present invention.

As shown in FIG. 11, the molding and filling portion 21 includes a mold 23, a blow nozzle 62, a valve block 63, an extension rod 64 and a pressure apparatus 65. The molding and filling portion 21 further includes a driving portion 66 that drives the molding and filling portion 21. In order to ensure the aseptic condition of the preform 1 and the bottle 2, the molding and filling portion 21 has to be cleaned and sterilized before starting operation, and the aseptic condition has to be maintained throughout the operation. Although not shown, the driving portion 66 includes a motor, a hydraulic unit, a motion transmitting device, an air cylinder and the like. The components of the driving portion 66 require lubricant and get dirty over time, so that it is difficult to keep the aseptic condition of the components.

As shown in FIG. 11, to ensure the aseptic condition of the molding and filling portion 21, the molding and filling portion 21 is shielded by the molding and filling portion chamber 22. The molding and filling portion chamber 22 is provided with a cleaning apparatus that cleans the interior of the molding and filling portion chamber 22 before the aseptic filling machine starts operating and a sterilizing apparatus that sterilizes the interior of the molding and filling portion chamber 22 before the aseptic filling machine starts operating. As shown in FIG. 11, the molding and filling portion chamber 22 is composed of a movable portion 67 that holds the molding and filling portion 21 and isolates the molding and filling portion 21 from the driving portion 66, and a fixed portion 68 that shields the molding and filling portion 21 from the outside. The movable portion 67 rotates about a double pipe 69. The molding and filling portion 21 held by the movable portion 67 also rotates, and the preform 1 is molded into the bottle 2 and at the same time filled with a content as the molding and filling portion 21 rotates.

By the mold 23 being closed, the preform 1 is passed from the wheel 17 to the molding and filling wheel 20. After that, the blow nozzle 62 is joined to the mouth portion 1a of the preform 1, the extension rod 64 is inserted into the preform 1 by being guided by a hole formed in the blow nozzle 62, and the extension rod 64 expands the preform 1 in the lengthwise direction until the bottom surface of the preform 1 comes into contact with the bottom surface of the mold 23. After that, the extension rod is lifted, and at the same time, a medium-pressure content P1 and then a high-pressure content P2 are successively fed into the preform 1 by the action of an electromagnetic valve of the valve block 63, thereby molding the preform 1 into the bottle 2 and at the same time filling the preform 1 with the contents. The high-pressure content P2 has to be fed until the preform 1 is completely molded into the shape of the mold 23. For this reason, the high-pressure content P2 fills the bottle 2 to the lower end of the mouth portion 1a. If the bottle 2 is filled to close to the upper end of the mouth portion 1a, the content can spill from the bottle 2 while the bottle 2 molded and filled is being conveyed. The amount of the high-pressure content P2 filling the bottle 2 has to be controlled to close to the lower end of the mouth portion 1a. The pressure of the medium-pressure content P1 is 1 MPa to 2.5 MPa, and the pressure of the high-pressure content P2 is 2.5 MPa to 4 MPa. As shown in FIG. 11, the medium-pressure content P1 and the high-pressure content P2 are obtained by the pressure apparatus 65 pressurizing the sterilized content from a sterilizing apparatus (not shown). The pressure apparatus is a multiple high-pressure plunger pump, for example.

When the mold 23 is opened, the molded bottle 2 is gripped by the gripper 34 on a wheel 24 and conveyed from the molding and filling portion 21 to a wheel 25 in the sealing portion 26. The molding of preforms 1 into bottles 2 and the filling thereof performed at the same time are performed by repeating opening and closing of the mold 23, which occur as the movable portion 67 of the molding and filling portion chamber 22 and the molding and filling portion 21 held on the movable portion 67 rotate, lowering and lifting of the extension rods 64, and filling of the preform 1 with the medium-pressure content P1 and the high-pressure content P2.

As shown in FIG. 11, an aseptic atmosphere is retained in the molding and filling portion chamber 22 throughout the operation of the aseptic filling machine. The driving portion 66 is provided in a non-aseptic atmosphere. The aseptic atmosphere and the non-aseptic atmosphere are isolated by a liquid seal apparatus 70, which is provided at the lower part of the movable portion 67, sealing the movable portion 67 at the lower part thereof. The liquid may be any liquid such as water. However, a liquid containing a sterilizer such as peracetic acid (the concentration of which is preferably equal to or higher than 100 ppm and equal to or lower than 3000 ppm) or a hydrogen peroxide (the content of which is preferably equal to or higher than 1% by mass and equal to or lower than 36% by mass) is preferably used. An end part of the movable portion 67 that is immersed in the liquid of the liquid seal apparatus 70 is provided so as not to come into contact with the bottom of the liquid seal apparatus 70. The liquid is in contact with the opposite surface of the immersed end part of the movable portion 67. However, when the aseptic air is supplied into the molding and filling portion chamber 22 and the pressure in the molding and filling portion chamber 22 is a positive pressure, the liquid level of the liquid seal apparatus 70 on the side of the non-aseptic atmosphere is higher than the liquid level on the side of the aseptic atmosphere.

As shown in FIG. 11, the medium-pressure content P1 and the high-pressure content P2 required to mold the preform 1 into the bottle 2 and at the same time fill the bottle 2 are supplied from above the molding and filling portion 21 through piping in the double pipe 69. The double pipe 69 and the fixed portion 68 are joined to each other by a rotary joint 71. The medium-pressure content P1 and the high-pressure content P2 are introduced into a high-pressure content supply manifold 72 in the non-aseptic atmosphere through the piping in the double pipe 69, which passes through the aseptic atmosphere. The medium-pressure content P1 and the high-pressure content P2 are supplied from the high-pressure content supply manifold 72 to the valve block 63 held on the movable portion 67, and therefore, the high-pressure content supply manifold 72 can rotate.

The interior of the molding and filling portion chamber 22 is cleaned before the aseptic filling machine starts operating. To this end, the molding and filling portion chamber 22 is provided with a cleaning apparatus. As shown in FIG. 11, the cleaning apparatus includes a blasting nozzle 56 provided on the fixed portion 68 of the molding and filling portion chamber 22 and a cleaner supplying apparatus that supplies a cleaner to the blasting nozzle 56. The blasting nozzle is a single-fluid spray or a twin-fluid spray that mixes the cleaner with compressed air and sprays the mixture. The cleaner is blasted from the blasting nozzle 56 into the molding and filling portion chamber 22 before the interior and the inner surface of the molding and filling portion chamber 22 are sterilized or at the same time as the sterilization. After that, water or aseptic water is blasted from the blasting nozzle 56 into the molding and filling portion chamber 22 to wash away the cleaner.

The mold 23 is opened in a limited area. To clean the interior of the mold 23, many blasting nozzles 56 are desirably provided in the area in which the mold is open (that is, the short section between the wheels 17 and 24). Further, when cleaning the mold 23, the cleaner is preferably blasted to the mold 23 while the mold 23 is rotated at a speed equal to or lower than 60 rpm. In this cleaning, the outer surface of the mold 23, the blow nozzle 62, an extension rod chamber 64a, the valve block 63 and the like in the molding and filling portion chamber 22 and the inner surface of the molding and filling portion chamber 22 are cleaned. The blasting pressure of the cleaner is at least equal to or higher than 0.05 MPa, and is preferably equal to or higher than 0.2 MPa.

As shown in FIG. 11, the extension rod 64 is held by an extension rod holding member 73. The lifting and lowering operations of the extension rod 64 are achieved by moving the extension rod holding member 73. The extension rod holding member 73 is moved vertically by the movement of the extension rod holding member motion shaft 73a. The extension rod holding member 73 is moved by a servomotor that rotates an extension rod holding member motion shaft 73a or a pneumatic cylinder coupled to the extension rod holding member motion shaft 73a. However, when the pneumatic cylinder is used, the interior of the cylinder needs to be sterilized by introducing a sterilizer gas into the cylinder, for example, and the air that produces pressure needs to be sterilized by passing the air through an aseptic filter. Further, a shaft that comes in and out of the pneumatic cylinder may be protected by a bellows. The extension rod 64 may not be directly held by the extension rod holding member 73 and may be lifted and lowered by means of a magnetic body.

The extension rod 64 is inserted into the blow nozzle 62, and the content is charged into the preform 1 along the outer periphery of the extension rod 64, so that the extension rod 64 comes into contact with the content. To prevent the content adhering to the extension rod 64 from being scattered in the molding and filling portion chamber 22, the extension rod 64, the extension rod holding member 73 and the extension rod holding member motion shaft 73a are shielded by an extension rod chamber 64a. Therefore, the extension rod 64, the extension rod holding member 73 and the extension rod holding member motion shaft 73a are cleaned by blasting the cleaner from the blasting nozzle 56 provided in the extension rod chamber 64a to the extension rod 64, the extension rod holding member 73 and the extension rod holding member motion shaft 73a. The extension rod chamber 64a has a cylindrical shape, for example. However, the extension rod chamber 64a can have any shape as far as the extension rod chamber 64a can shield the extension rod 64, the extension rod holding member 73 and the extension rod holding member motion shaft 73a.

While the extension rod 64 is inserted in the blow nozzle 62, the inserted part of the extension rod 64 cannot be cleaned. For this reason, the extension rod 64 is cleaned while the extension rod 64 is not inserted in the blow nozzle. Therefore, the extension rod 64 is driven by the extension rod holding member 73 and the extension rod holding member motion shaft 73a in such a manner that the extension rod 64 is lifted to a position where the extension rod 64 is completely retracted from the blow nozzle 62. FIG. 11 shows the preform 1 with the mouth portion facing upward, the preform 1 may be inverted. In that case, the extension rod 64 is moved downward and retracted from the blow nozzle 62.

The cleaner is water containing an acidic compound or a basic compound. The water may be water or pure water sterilized by heating or filtering, ion-exchanged water, distilled water, or tap water. The acidic compound may be an inorganic acid such as hydrochloric acid, nitrous acid, or phosphoric acid, or an organic acid such as acetic acid, formic acid, octanic acid, oxalic acid, citric acid, succinic acid, or gluconic acid. The basic compound may be an inorganic basic compound such as sodium hydroxide or potassium hydroxide, or organic basic compound such as ethanolamine or diethylamine. Further, the cleaner may contain a sequestering agent such as an alkali metal salt, an alkaline-earth metal salt, an ammonium salt of an organic acid or ethylenediaminetetraacetic acid, a nonionic surface active agent such as an anionic surface active agent, a cationic surface active agent, or polyoxyethylene alkyl phenyl ether, a solubilizing agent such as sodium cumenesulfonate, an acidic polymer such as polyacrylic acid or a metal salt thereof, a corrosion inhibitor, an antiseptic agent, an antioxidant, a dispersant, or an antifoaming agent, for example. If such a cleaning liquid is heated to a temperature equal to or higher than 50° C., the cleaning liquid has a sterilization effect. Therefore, the heated cleaning liquid may also be used as a sterilizer for sterilizing the interior of the molding and filling portion chamber 22.

After the interior and the inner surface of the molding and filling portion chamber 22 are cleaned, or at the same time as the cleaning, the interior and the inner surface of the molding and filling portion chamber 22 are sterilized. The sterilizer is blasted from the blasting nozzle 56 into the molding and filling portion chamber 22. To this end, the molding and filling portion chamber 22 is provided with a sterilizing apparatus. As shown in FIG. 11, the sterilizing apparatus includes at least a blasting nozzle 56 provided on the fixed portion 68 of the molding and filling portion chamber 22, and a sterilizer supplying unit that supplies the sterilizer to the blasting nozzle 56. The nozzle for blasting the cleaner may double as the blasting nozzle 56, or another nozzle may be provided as the blasting nozzle 56. The sterilizer is blasted in such a manner that the sterilizer comes into contact with the entire surface in the molding and filling portion chamber 22. The sterilizer blasted sterilizes the interior of the molding and filling portion chamber 22. The blasting nozzle 56 is arranged so that the sterilizer comes into contact with the entire surface in the molding and filling portion chamber 22.

The mold 23 is opened in a limited area. To sterilize the interior of the mold 23, many blasting nozzles 56 are desirably provided in the area in which the mold is open (that is, the short section between the wheels 17 and 24). Further, when sterilizing the mold 23, the sterilizer is preferably blasted to the mold 23 while the mold 23 is rotated at a speed equal to or lower than 60 rpm. In this sterilization, the mold 23, the blow nozzle 62, the extension rod 64, the valve block 63 and the like in the molding and filling portion chamber 22 and the inner surface of the molding and filling portion chamber 22 are sterilized. The blasting pressure of the sterilizer is at least equal to or higher than 0.05 MPa, and is preferably equal to or higher than 0.2 MPa.

The extension rod 64, the extension rod holding member 73, the extension rod holding member motion shaft 73a, and the interior of the extension rod chamber 64a are sterilized by the sterilizer blasted from the blasting nozzle 56 provided in the extension rod chamber 64a. The sterilization is also performed while the extension rod 64 is not inserted in the blow nozzle 62.

The sterilizer may be the same as the sterilizer used for sterilizing the preform 1, and is preferably a sterilizer containing peracetic acid or hydrogen peroxide. Different kinds of sterilizers may be blasted in a plurality of steps.

After the sterilizer is blasted from the blasting nozzle 56, aseptic water is blasted to the entire area of the molding and filling portion chamber 22 from the same blasting nozzle 56 or a different nozzle. The aseptic water washes away the sterilizer remaining in the molding and filling portion chamber 22. The aseptic water is produced by sterilizing water by heating the water to a temperature equal to or higher than 121° C. for four or more minutes or passing the water through an aseptic filter. The aseptic water blasted into the molding and filling portion chamber 22 is preferably heated to a temperature from 60° C. to 100° C.

After the aseptic water is blasted into the molding and filling portion chamber 22, aseptic air is blasted into the molding and filling portion chamber 22. The aseptic air vaporizes and removes the aseptic water remaining in the molding and filling portion chamber 22. To blast the aseptic air into the molding and filling portion chamber 22, as shown in FIG. 11, an aseptic air supplying apparatus 57 is provided on top of the fixed portion 68 of the molding and filling portion chamber 22. The aseptic air supplying apparatus 57 includes a blower 58 and an aseptic filter 59. The aseptic air may be heated, and an aseptic air heating apparatus 60 is preferably provided between the blower 58 and the aseptic filter 59.

Air from the blower 58 is heated by the heating apparatus 60 and sterilized by the aseptic filter 59, and the resulting aseptic hot air is blasted into the molding and filling portion chamber 22. Although the aseptic air may not be heated, the heated aseptic air removes the aseptic water in a shorter time. The molding and filling portion chamber 22 may not be provided with the aseptic air supplying apparatus, and the heated aseptic air discharged from the heating portion chamber 18 may be blasted into the molding and filling portion chamber 22. When the aseptic air is supplied to the molding and filling portion chamber 22 during operation of the aseptic filling machine in order to maintain the aseptic condition in the molding and filling portion chamber 22, the aseptic air may not be heated.

The cleaning and sterilization of the interior of the molding and filling portion chamber 22 occur in the following procedure, for example. That is, a cleaner containing sodium hydroxide, which is a basic compound, is blasted into the molding and filling portion chamber 22 and then washed away by blasting aseptic water, a sterilizer containing peracetic acid is blasted into the molding and filling portion chamber 22 and then washed away by blasting aseptic water, a gas or mist of a hydrogen peroxide solution or a mixture thereof used for sterilization of preforms is blasted into the molding and filling portion chamber 22, and then heated aseptic air is supplied to dry the interior of the molding and filling portion chamber 22 to complete the sterilization.

When the gas or mist of hydrogen peroxide or a mixture thereof is blasted into the molding and filling portion chamber 22, if the temperature of the outer surface of the blow nozzle 62 and the valve block 63, which is exposed in the molding and filling portion chamber 22 for cleaning and sterilization of the flow path in the blow nozzle 62, is equal to or higher than 60° C., and the outer surface is exposed to a hydrogen peroxide gas having a concentration of 5 mg/L or higher, the outer surface is appropriately sterilized.

In the sterilization before operation of the aseptic filling machine, the inner surface of the aseptic filter 59 is also sterilized since the sterilizer is blasted from the blasting nozzle 56.

The aseptic air having passed through the aseptic filter 59 may be blasted into the molding and filling portion chamber 22 and discharged by the exhaust apparatus 61 provided on the molding and filling portion chamber 22. The aseptic air may flow from the molding and filling portion chamber 22 into the heating portion chamber 18 and be discharged by the exhaust apparatus provided on the heating portion chamber 18.

Components exposed in the molding and filling portion chamber 22 are cleaned and sterilized by blasting the cleaner and the sterilizer into the molding and filling portion chamber 22. However, the interior of the piping for the medium-pressure content P1 and the high-pressure content P2 in the blow nozzle 62 and the valve block 63, which is not exposed, is not cleaned and sterilized. Therefore, before the aseptic filling machine starts operating, cleaning (CIP) and sterilization (SIP) of the interior of the piping are performed.

Figure 12:
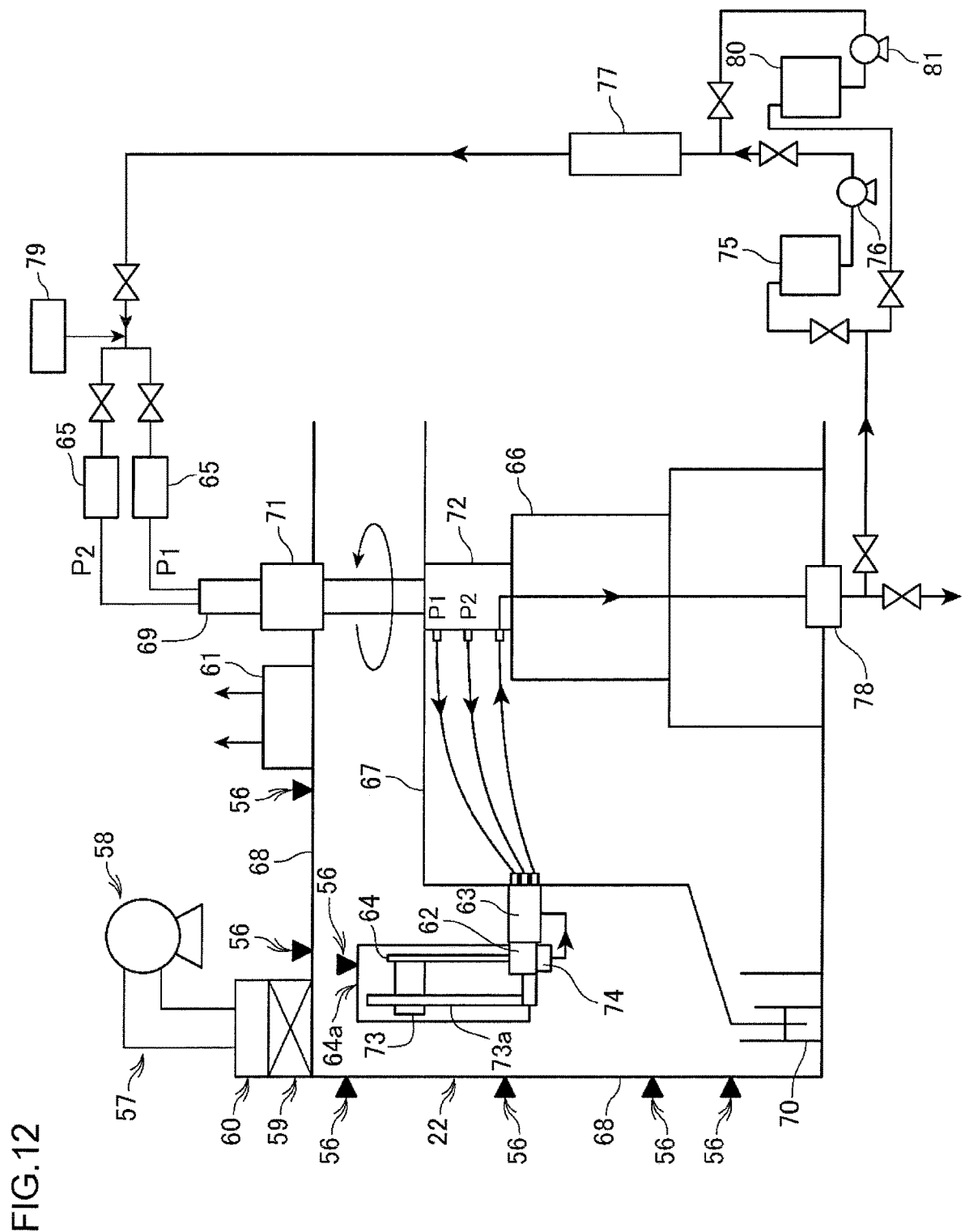
FIG. 12 shows an apparatus that performs CIP and SIP in the preform molding and filling portion according to the embodiment of the present invention.

As shown in FIG. 12, CIP is performed with a cup-shaped closure apparatus 74 attached on a tip end of the blow nozzle 62. A cleaner tank 75 is provided, and the cleaner in the cleaner tank 75 is delivered under pressure by a cleaner supply pump 76, is heated by a heating apparatus 77 as required, passes through the pressure apparatus 65, and is fed to the valve block 63, the blow nozzle 62 and then the extension rod 64. The cleaner discharged from the blow nozzle is received by the cup-shaped closure apparatus 74 attached to the tip end of the blow nozzle 62, passes through a path in the valve block 63, flows into the high-pressure content supply manifold 72, and returns to the cleaner tank 75 through piping in a pipe body provided in the middle of the driving portion 66 via a rotary joint 78 provided at the bottom of the driving portion 66. CIP is performed by circulating the cleaner in the circulation path as described above. The sequence of the components in the circulation path can be appropriately changed as far as all the parts to come into contact with the content can be cleaned.

The cleaner is the same cleaner as that used for cleaning the interior of the molding and filling portion chamber 22. Some cleaners have a sterilization effect when they are heated to a temperature equal to or higher than 50° C., and such cleaners may be heated by the heating apparatus 77.

As shown in FIG. 12, SIP is performed by a heated vapor supplying apparatus 79 supplying heated vapor to the pressure apparatus 65. The heated vapor supplied to the pressure apparatus 65 is supplied to the blow nozzle 62 and the extension rod 64 via the high-pressure content supply manifold 72 and the valve block 63. The heated vapor discharged from the blow nozzle 62 is further received by the cup-shaped closure apparatus 74 attached to the tip end of the blow nozzle 62 and discharged from the bottom of the driving portion 66. SIP is achieved by the heat of the heated vapor. The heated vapor is supplied at a temperature equal to or higher than 121° C.

SIP may also be achieved with hot water. In the SIP with hot water, as shown in FIG. 12, aseptic water is delivered under pressure from an aseptic water tank 80 by an aseptic water supply pump 81. The aseptic water delivered under pressure is heated by the heating apparatus 77 to a temperature from 70° C. to 100° C., and delivered to the valve block 63 and then to the blow nozzle 62 via the pressure apparatus 65. The aseptic water discharged from the blow nozzle is received by the cup-shaped closure apparatus 74 attached to the tip end of the blow nozzle 62, passes through the path in the valve block 63, flows into the high-pressure content supply manifold 72, and returns to the aseptic water tank 80 through the piping in the pipe body provided in the middle of the driving portion 66 via the rotary joint 78 provided at the bottom of the driving portion 66. SIP is performed by circulating the hot water in the circulation path as described above. The heating apparatus 77 may be another heating apparatus provided in addition to the heating apparatus used for heating the cleaner. The sequence of the components in the circulation path can be appropriately changed as far as all the parts to come into contact with the product liquid can be sterilized.

The bottle 2 filled with the content is conveyed to the sealing portion 26 via the wheel 24 shown in FIG. 1. The bottle 2 is conveyed to the sealing wheel 25 provided in the sealing portion 26. In the sealing step shown in FIG. 13, a cap 35 sterilized by a cap sterilizing apparatus 28 is supplied to the sealing wheel 25, and a capper (not shown) fits the cap 35 on the mouth portion 1*a* of the bottle 2 to seal the bottle 2.

The sealed bottle 2 is passed from the gripper 34 on the sealing wheel 25 to the gripper 34 on a discharging wheel 29 in the discharging portion 30. The bottle 2 passed to the discharging wheel 29 is placed on a discharging conveyor 31. The bottle 2 placed on the discharging conveyor 31 is discharged from inside the sealing portion chamber 27 to the outside of the aseptic filling machine.

Before the aseptic filling machine starts operating, the interior of the sealing portion chamber 27 is subjected to cleaning by blasting a cleaner, cleaning by blasting aseptic water, sterilization by blasting a sterilizer, removal of the sterilizer by blasting aseptic water, removal of the aseptic water by blasting aseptic air and other operations, as with the molding and filling portion chamber 22. Further, during operation of the aseptic filling machine, the aseptic condition in the sealing portion chamber 27 is maintained by an aseptic air supplying apparatus provided on the sealing portion chamber 27 supplying aseptic air to keep a positive pressure in the sealing portion chamber 27. To keep an appropriate pressure in the sealing portion chamber 27, the sealing portion chamber 27 may be provided with an exhaust apparatus. Thus, the sealing portion chamber 27 is provided with at least a sterilizing apparatus that sterilizes the interior and the inner surface of the sealing portion chamber 27 and an aseptic air supplying apparatus that supplies aseptic air into the sealing portion chamber 27. The sealing portion chamber 27 is also provided with a cleaning apparatus that cleans the interior of the sealing portion chamber 27.

In the following, a second embodiment of the present invention of this application will be described with reference to FIG. 14.

Second Embodiment

An aseptic filling machine according to the second embodiment will be first schematically described with reference to FIG. 14. The aseptic filling machine includes a heating portion 14 that heats a preform 1 supplied from a preform supplying apparatus 3 to a temperature for molding the preform 1 into a bottle 2, a post-heating sterilizing portion 82 that sterilizes the heated preform 1, a molding and filling portion 21 that fills the sterilized preform 1 with a sterilized content under high pressure, thereby molds the preform 1 into the bottle 2 and at the same time fills the bottle 2 with a content, and a sealing portion 26 that seals the bottle 2 filled with the content. According to the second embodiment, the sterilized preform 1 can be filled with the content while being molded, and an aseptic product filled with a content can be produced with a reduced number of steps compared with prior art.

(Aseptic Filling Machine and Aseptic Filling Method According to Second Embodiment)

Figure 14:
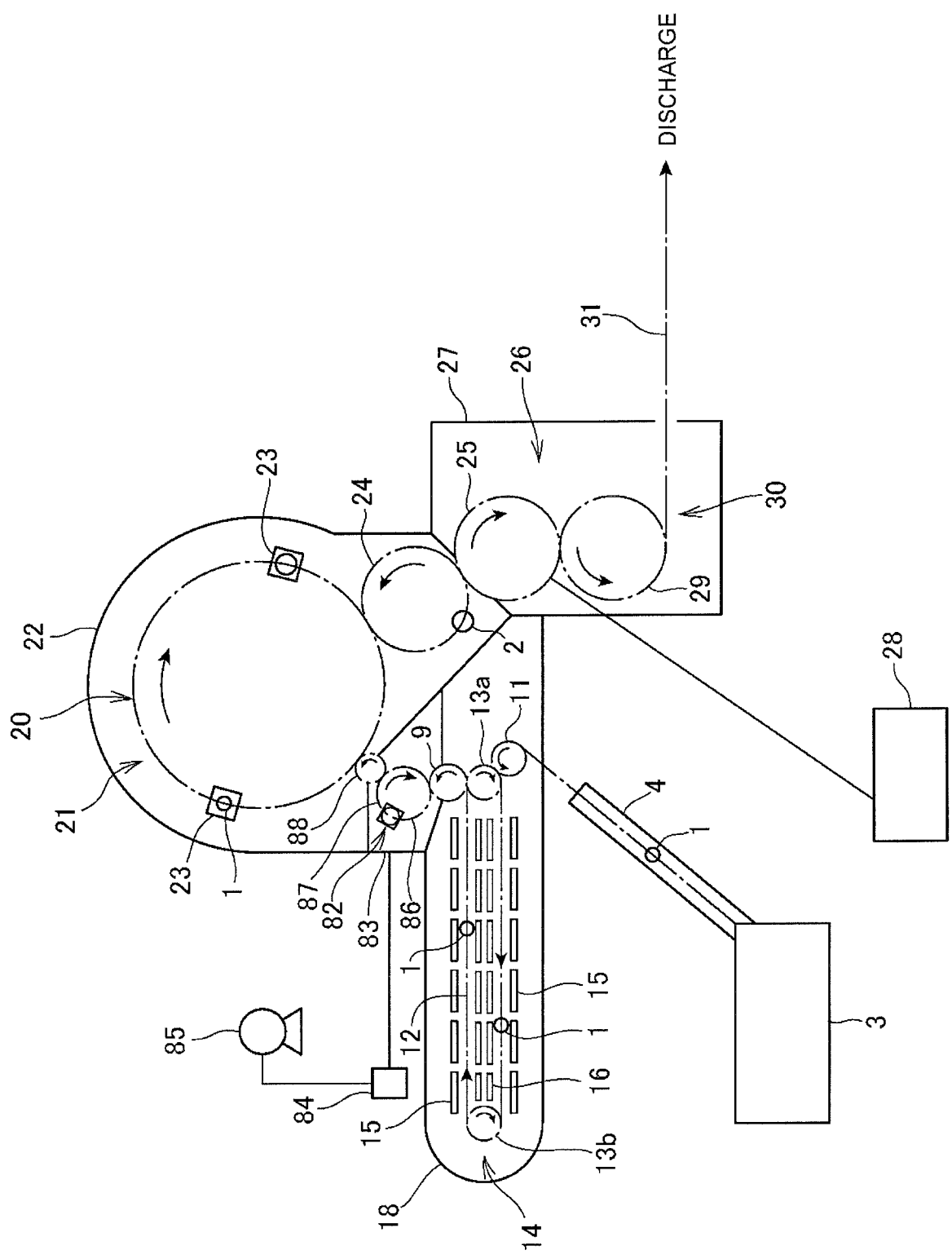
FIG. 14 is a plan view schematically showing an example of an aseptic filling machine according to a second embodiment of the present invention.

As shown in FIG. 14, the aseptic filling machine according to this embodiment includes the preform supplying apparatus 3 that supplies the preform 1, the heating portion 14 that heats the preform 1 to a temperature for molding the preform 1 into the bottle 2, the post-heating sterilizing portion 82 that sterilizes the heated preform 1, the molding and filling portion 21 that molds the preform 1 into the bottle 2 and at the same time fills the bottle 2 with a sterilized content, and the sealing portion 26 that seals the bottle 2 filled with the content with a sterilized cap 35. The aseptic filling machine further includes a discharging portion 30 in which the sealed bottle 2 is placed on a discharging conveyor 31 and discharged to a non-aseptic zone.

The heating portion 14 is shielded by a heating portion chamber 18, the post-heating sterilizing portion 82 is shielded by a post-heating sterilizing portion chamber 83, the molding and filling portion 21 is shielded by a molding and filling portion chamber 22, and the sealing portion 26 and the discharging portion 30 are shielded by a sealing portion chamber 27. The heating portion 14 is located upstream of the post-heating sterilizing portion 82, and may be shielded by no chamber because the heating portion 14 is located in a non-aseptic area. The molding and filling portion 21 and the sealing portion 26 may be shielded by a single chamber. Depending on the sterilizing device for the preform 1 in the post-heating sterilizing portion 82, a gas or mist of a sterilizer, a mixture thereof, or ozone can be produced in the post-heating sterilizing portion chamber 83. To prevent these from flowing into the heating portion 14, the gas in the post-heating sterilizing portion 82 is discharged by an exhaust gas blower 85 through an exhaust gas processing apparatus 84 that detoxifies the gas or mist of the sterilizer, a mixture thereof, or ozone.

Of the post-heating sterilizing portion chamber 83, the molding and filling portion chamber 22 and the sealing portion chamber 27, at least the molding and filling portion chamber 22 and the sealing portion chamber 27 are provided with a sterilizing apparatus, and the interior of each of the chambers is sterilized before the aseptic filling machine starts operating. The interior of the post-heating sterilizing portion chamber 83 can be sterilized when the preform 1 is sterilized, and therefore does not need to be sterilized before the aseptic filling machine starts operating. The heating portion 14 is located upstream of the post-heating sterilizing portion 82, and the interior of the heating portion chamber 18 does not need to be sterilized.

At least the sterilizing apparatuses provided on the molding and filling portion chamber 22 and the sealing portion chamber 27 are the same as those according to the first embodiment. Further, at least the aseptic air supplying apparatuses provided on the molding and filling portion chamber 22 and the sealing portion chamber 27 are also the same as those according to the first embodiment.

Preforms such as the preform 1 shown in FIG. 2 are successively conveyed from the preform supplying apparatus 3 shown in FIG. 14 to the heating portion 14 at a desired speed by a preform supply conveyor 4.

The preform 1 according to the second embodiment of the present invention is the same as that according to the first embodiment.

As shown in FIG. 14, the preform 1 is supplied from the preform supplying apparatus 3 to the heating furnace conveying wheel 11 by the preform supply conveyor 4. The preform 1 supplied to the heating furnace conveying wheel 11 is gripped at the support ring 1*b* thereof by a gripper 34 provided on the heating furnace conveying wheel 11 as shown in FIG. 2. After that, the preform 1 is released from the gripper 34, a spindle 52 is inserted into the mouth portion 1*a* of the preform 1, and then the preform 1 is conveyed to the heating portion 14. The preform 1 conveyed to the heating portion 14 is heated to a temperature suitable for the subsequent blow molding by an infrared heater 15 or other heating device. A reflector 16 is provided on the opposite side of the preform 1 to the infrared heater 15, and the heat emitted from the infrared heater 15 is reflected by the reflector 16 to efficiently heat the preform 1. The preform 1 is preferably heated to a temperature from 90° C. to 130° C. The temperature of the mouth portion 1a of the preform 1 is kept to be equal to or lower than 70° C., in order to prevent deformation or the like of the mouth portion 1a.

The preform 1 is conveyed in the heating portion 14 while being rotated with the spindle 52 inserted in the mouth portion 1a. Spindles 52 are provided on an endless chain 12 at regular intervals. The endless chain 12 rotates on pulleys 13a and 13b. Instead of the spindle 52, a mandrel may be inserted into the preform 1 to rotate and convey the preform 1 in the inverted position.

The heated preform 1 is released from the spindle 52, gripped by the gripper 34 and conveyed to a post-heating sterilizing wheel 86 in the post-heating sterilizing portion 82 via a wheel 9.

The preform 1 conveyed to the post-heating sterilizing portion 82 is conveyed to the post-heating sterilizing wheel 86, on which a large number of grippers 34 is provided at regular pitches, and is sterilized on the wheel 86. A post-heating sterilization step of sterilizing the preform 1 is achieved by any one or more of contact with a gas or mist of a sterilizer or a mixture thereof, irradiation with an electron beam, irradiation with light containing ultraviolet radiation, and contact with overheated vapor. The post-heating sterilizing wheel 86 is provided with a post-heating sterilizing device 87 for performing the post-heating sterilization step. The preform 1 is heated to the molding temperature in the heating portion 14, and is more effectively sterilized than when the preform 1 is at room temperature.

The contact of the preform 1 with a gas or mist of a sterilizer or a mixture thereof, the irradiation of the preform 1 with an electron beam, the irradiation of the preform 1 with light containing ultraviolet radiation, and the contact of the preform 1 with overheated vapor, which are performed as the post-heating sterilization step, are the same as those according to the first embodiment. In the post-heating sterilizing portion 82, the preform 1 is sterilized by the post-heating sterilizing device 87 provided on the post-heating sterilizing wheel 86 in any one or more processes selected from among contact with a gas or mist of a sterilizer or a mixture thereof, irradiation with an electron beam, irradiation with light containing ultraviolet radiation, and contact with overheated vapor. Although the post-heating sterilizing device 87 is provided around the post-heating sterilizing wheel 86, one or more wheels may be provided in addition to the post-heating sterilizing wheel 86, and a plurality of wheels may be provided with a sterilizing device.

Before the aseptic filling machine starts operating, the interior of the post-heating sterilizing portion chamber 83 may be sterilized by spraying a sterilizer such as a hydrogen peroxide solution into the post-heating sterilizing portion chamber 83, for example. To this end, a sterilizer blasting nozzle is provided on an inner wall surface of the post-heating sterilizing portion chamber 83. Further, a similar sterilizer blasting nozzle may be provided to sterilize the surface of the aseptic filter of the aseptic air supplying apparatus, which is adjacent to the post-heating sterilizing portion chamber 83, that is closer to the post-heating sterilizing portion chamber 83.

The preform 1 sterilized in the post-heating sterilizing portion 82 is conveyed, with the support ring 1b thereof gripped, to a molding and filling wheel 20 in the molding and filling portion 21 via a wheel 88. In the same molding and filling step as in the first embodiment, a sterilized content is charged under high pressure into the preform 1 conveyed to the molding and filling wheel 20, thereby molding the preform 1 into the bottle 2 and at the same time filling the bottle 2 with the content. The bottle 2 molded and filled is sealed in the sealing portion 26 in the same manner as in the first embodiment.

In the following, a third embodiment of the present invention of this application will be described with reference to FIG. 15.

Third Embodiment

An aseptic filling machine according to the third embodiment will be first schematically described with reference to FIG. 15, and then differences from the first and second embodiments will be described. The aseptic filling machine includes a pre-heating sterilizing portion 6 that sterilizes a preform 1 supplied from a preform supplying apparatus 3, a heating portion 14 that heats the sterilized preform 1 to a temperature for molding the preform 1 into a bottle 2, a post-heating sterilizing portion 82 that sterilizes the heated preform 1, a molding and filling portion 21 that fills the sterilized preform 1 with a sterilized content under high pressure, thereby molding the preform 1 into the bottle 2 and at the same time filling the bottle 2 with the content, and a sealing portion 26 that seals the bottle 2 filled with the content. According to the third embodiment, since the preform 1 is sterilized before heated, the sterilization after heating can be simplified, so that the preform 1 can be molded and at the same time filled with the content while preventing the temperature of the heated preform 1 from lowering, and an aseptic product which is a bottle 2 filled with a content can be produced with a reduced number of steps compared with prior art.

(Aseptic Filling Machine and Aseptic Filling Method According to Third Embodiment)

Figure 15:
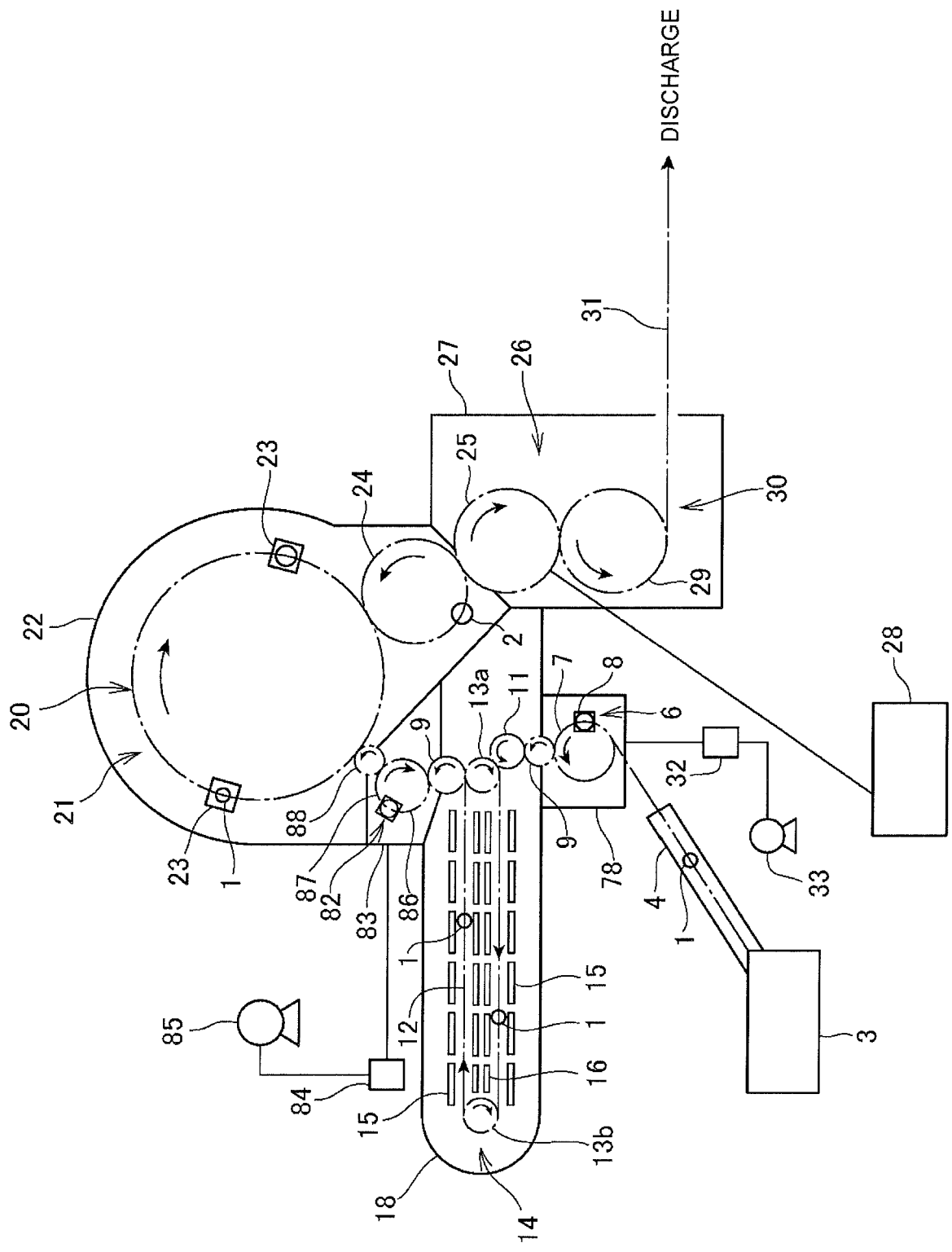
FIG. 15 is a plan view schematically showing an example of an aseptic filling machine according to a third embodiment of the present invention.

As shown in FIG. 15, the aseptic filling machine according to the third embodiment includes the preform supplying apparatus 3 that supplies the preform 1, the pre-heating sterilizing portion 6 that sterilizes the preform 1, the heating portion 14 that heats the preform 1 to a temperature for molding the preform 1 into the bottle 2, the post-heating sterilizing portion 82 that sterilizes the heated preform 1, the molding and filling portion 21 that molds the preform 1 into the bottle 2 and at the same time fills the bottle 2 with a sterilized content, and the sealing portion 26 that seals the bottle 2 filled with the content with a sterilized cap 35. The aseptic filling machine further includes a discharging portion 30 in which the sealed bottle 2 is placed on a discharging conveyor 31 and discharged to a non-aseptic zone.

The pre-heating sterilizing portion 6 is shielded by a pre-heating sterilizing portion chamber 5, the heating portion 14 is shielded by a heating portion chamber 18, the post-heating sterilizing portion 82 is shielded by a post-heating sterilizing portion chamber 83, the molding and filling portion 21 is shielded by a molding and filling portion chamber 22, and the sealing portion 26 and the discharging portion 30 are shielded by a sealing portion chamber 27. The heating portion 14 is not located in the aseptic area, and does not need to be shielded. Depending on the sterilizing device for the preform 1 in the pre-heating sterilizing portion 6, a gas or mist of a sterilizer, a mixture thereof, or ozone can be produced in the pre-heating sterilizing chamber 5 or post-heating sterilizing portion chamber 83. To prevent these from flowing into the heating portion 14, the gas in the pre-heating sterilizing portion 6 is discharged by an exhaust gas blower 33 through an exhaust gas processing apparatus 32 that detoxifies the gas or mist of the sterilizer, a mixture thereof, or ozone. The other chambers are the same as those according to the second embodiment.

Of the pre-heating sterilizing portion chamber 5, the heating portion chamber 18, the post-heating sterilizing portion chamber 83, the molding and filling portion chamber 22 and the sealing portion chamber 27, at least the molding and filling portion chamber 22 and the sealing portion chamber 27 are provided with a sterilizing apparatus, and the interior of each of the chambers is sterilized before the aseptic filling machine starts operating. The interior of the pre-heating sterilizing portion chamber 5 and the post-heating sterilizing portion chamber 83 can be sterilized when the preform 1 is sterilized, and therefore does not need to be sterilized before the aseptic filling machine starts operating. The heating portion 14 is located upstream of the post-heating sterilizing portion 82, and the interior of the heating portion chamber 18 does not need to be sterilized.

At least the sterilizing apparatuses provided on the molding and filling portion chamber 22 and the sealing portion chamber 27 are the same as those according to the first embodiment. Further, at least the aseptic air supplying apparatuses provided on the molding and filling portion chamber 22 and the sealing portion chamber 27 are also the same as those according to the first embodiment.

(Details of Aseptic Filling Machine and Aseptic Filling Method According to Third Embodiment)

Preforms such as the preform 1 shown in FIG. 2 are successively conveyed from the preform supplying apparatus 3 shown in FIG. 15 to the pre-heating sterilizing portion 6 at a desired speed by a preform supply conveyor 4. The preform 1 is the same as that according to the first embodiment.

The preform 1 conveyed to the pre-heating sterilizing portion 6 is passed to a pre-heating sterilizing wheel 7 on which a large number of grippers 34 is provided at regular pitches, and is sterilized on the wheel 7. A pre-heating sterilization step of sterilizing the preform 1 is achieved by any one or more of contact with a sterilizer, irradiation with an electron beam, irradiation with light containing ultraviolet radiation, contact with hot water, and contact with overheated vapor. The pre-heating sterilization step is the same as that according to the first embodiment. The pre-heating sterilizing wheel 7 is provided with a pre-heating sterilizing device 8 for performing the pre-heating sterilization step. The preform 1 may be preheated by hot air before the sterilization. To preheat the preform 1, a preheating wheel may be provided before the pre-heating sterilizing wheel 7. The sterilization effect is improved by preheating the preform 1.

As described above, in the pre-heating sterilizing portion 6, the preform 1 is sterilized by the pre-heating sterilizing device 8 provided on the pre-heating sterilizing wheel 7 in any one or more processes selected from among contact with a sterilizer, irradiation with an electron beam, irradiation with light containing ultraviolet radiation, contact with hot water, and contact with overheated vapor. Although the pre-heating sterilizing device 8 is provided around the pre-heating sterilizing wheel 7, one or more wheels may be provided in addition to the pre-heating sterilizing wheel 7, and a plurality of wheels may be provided with a pre-heating sterilizing device 8. Sterilization may be performed not only on the pre-heating sterilizing wheel 7 but also in the preform supplying apparatus 3 or on the preform supply conveyor 4.

The preform 1 sterilized in the pre-heating sterilizing portion 6 is gripped at the support ring 1b thereof by a gripper 34 and passed to the heating furnace conveying wheel 11 via a wheel 9. The preform 1 conveyed to the heating furnace conveying wheel 11 is heated in the heating portion 14 in the same process as in the first embodiment, the heated preform 1 is sterilized in the post-heating sterilizing portion 82, the sterilized preform 1 is molded into the bottle 2 and at the same time filled with a content in the molding and filling portion 21, the bottle 2 filled with the content is sealed in the sealing portion 26, and the sealed bottle 2 is discharged to the outside of the aseptic filling machine via a discharging portion 30. The post-heating sterilization step is the same as that in the second embodiment.

Although the present invention is configured as described above, the present invention is not limited to the embodiments described above. For example, although the aseptic filling machine has been described as a wheel-based aseptic filling machine, various alterations can be made without departing from the spirit of the present invention, and a linear aseptic filling machine is also possible, for example.

REFERENCE SIGNS LIST 1 preform
2 bottle
5 pre-heating sterilizing portion chamber
6 pre-heating sterilizing portion
8 pre-heating sterilizing device
14 heating portion
18 heating portion chamber
21 molding and filling portion
22 molding and filling portion chamber
23 mold
26 sealing portion
27 sealing portion chamber
57 aseptic air supplying apparatus
62 blow nozzle
63 valve block
64 extension rod
65 pressure apparatus
67 movable portion
68 fixed portion
72 high-pressure content supply manifold
74 closure apparatus
82 post-heating sterilizing portion
83 post-heating sterilizing portion chamber
87 post-heating sterilizing device
P1 medium-pressure content
P2 high-pressure content

The invention claimed is:

1. An aseptic filling machine, comprising a pre-heating sterilizing portion that sterilizes a preform, a heating portion that heats the sterilized preform, a molding and filling portion that fills the heated preform with a sterilized content under high pressure, thereby molding the preform into a bottle and at the same time filling the preform with the content, and a sealing portion that seals the bottle filled with the content, wherein the pre-heating sterilizing portion, the heating portion, the molding and filling portion and the sealing portion are each shielded by a chamber, a sterilizing apparatus and an aseptic air supplying apparatus are provided, and of a pre-heating sterilizing portion chamber that shields the pre-heating sterilizing portion, a heating portion chamber that shields the heating portion, a molding and filling portion chamber that shields the molding and filling portion and a sealing portion chamber that shields the sealing portion, the sterilizing apparatus sterilizes an interior and an inner surface of at least the molding and filling portion chamber and the sealing portion chamber, and the aseptic air supplying apparatus supplies aseptic air into at least the molding and filling portion chamber and the sealing portion chamber, the molding and filling portion includes at least a mold, a blow nozzle, an extension rod, a valve block and a pressure apparatus that pressurizes the content from 1 MPa to 4 MPa, a cup-shaped closure apparatus is provided for receiving a substance discharged from the blow nozzle, and a circulation path is provided from the cup-shaped closure apparatus to the pressure apparatus, the valve block, and the blow nozzle, and the circulation path is circulated with a cleaner or a hot water for cleaning and sterilizing of an interior of a piping for the contents.

2. The aseptic filling machine according to claim 1, wherein a cleaning apparatus is provided which cleans the interior of the molding and filling portion chamber and the sealing portion chamber.

3. The aseptic filling machine according to claim 1, wherein the molding and filling portion chamber includes a movable portion that holds the molding and filling portion and a fixed portion that shields the molding and filling portion from an outside air.

4. The aseptic filling machine according to claim 1, wherein a sterilizing device for the preform in the pre-heating sterilizing portion is configured to do any one or more of contact of the preform with a sterilizer, irradiation of the preform with an electron beam, irradiation of the preform with light containing ultraviolet radiation, contact of the preform with hot water, and contact of the preform with overheated vapor.

5. The aseptic filling machine according to claim 1, wherein the pressure apparatus is a high-pressure plunger pump.

6. The aseptic filling machine according to claim 1, wherein an extension rod shielding chamber that shields the extension rod is provided.

7. The aseptic filling machine according to claim 1, wherein an extension rod driving apparatus is provided which drives the extension rod to a position where the extension rod is not inserted in the blow nozzle.

8. An aseptic filling machine, comprising a heating portion that heats a preform, a post-heating sterilizing portion that sterilizes the heated preform, a molding and filling portion that fills the sterilized preform with a sterilized content under high pressure, thereby molding the preform into a bottle, and a sealing portion that seals the bottle filled with the content, wherein the post-heating sterilizing portion, the molding and filling portion and the sealing portion are each shielded by a chamber, a sterilizing apparatus and an aseptic air supplying apparatus are provided, and of a post-heating sterilizing portion chamber that shields the post-heating sterilizing portion, a molding and filling portion chamber that shields the molding and filling portion and a sealing portion chamber that shields the sealing portion, the sterilizing apparatus sterilizes an interior and an inner surface of at least the molding and filling portion chamber and the sealing portion chamber, and the aseptic air supplying apparatus supplies aseptic air into at least the molding and filling portion chamber and the sealing portion chamber, the molding and filling portion includes at least a mold, a blow nozzle, an extension rod, a valve block and a pressure apparatus that pressurizes the content from 1 MPa to 4 MPa, a cup-shaped closure apparatus is provided for receiving a substance discharged from the blow nozzle, and a circulation path is provided from the cup-shaped closure apparatus to the pressure apparatus, the valve block, and the blow nozzle, and the circulation path is circulated with a cleaner or a hot water for cleaning and sterilizing of an interior of a piping for the contents.

9. The aseptic filling machine according to claim 8, wherein a sterilizing device for the preform in the post-heating sterilizing portion is configured to do any one or more of contact of the preform with a gas or mist of a sterilizer or a mixture thereof, irradiation of the preform with an electron beam, irradiation of the preform with light containing ultraviolet radiation, and contact of the preform with overheated vapor.

10. The aseptic filling machine according to claim 8, wherein a cleaning apparatus is provided which cleans the interior of the molding and filling portion chamber and the sealing portion chamber.

11. The aseptic filling machine according to claim 8, wherein the molding and filling portion chamber includes a movable portion that holds the molding and filling portion and a fixed portion that shields the molding and filling portion from an outside air.

12. The aseptic filling machine according to claim 8, wherein the pressure apparatus is a high-pressure plunger pump.

13. The aseptic filling machine according to claim 8, wherein an extension rod shielding chamber that shields the extension rod is provided.

14. The aseptic filling machine according to claim 8, wherein an extension rod driving apparatus is provided which drives the extension rod to a position where the extension rod is not inserted in the blow nozzle.

15. An aseptic filling machine, comprising a pre-heating sterilizing portion that sterilizes a preform, a heating portion that heats the sterilized preform, a post-heating sterilizing portion that sterilizes the heated preform, a molding and filling portion that fills the heated preform with a sterilized content under high pressure, thereby molding the preform into a bottle and at the same time filling the preform with the content, and a sealing portion that seals the bottle filled with the content, wherein the pre-heating sterilizing portion, the heating portion, the post-heating sterilizing portion, the molding and filling portion and the sealing portion are each shielded by a chamber, a sterilizing apparatus and an aseptic air supplying apparatus are provided, and of a pre-heating sterilizing portion chamber that shields the pre-heating sterilizing portion, a heating portion chamber that shields the heating portion, a post-heating sterilizing portion chamber that shields the post-heating sterilizing portion, a molding and filling portion chamber that shields the molding and filling portion and a sealing portion chamber that shields the sealing portion, the sterilizing apparatus sterilizes an interior and an inner surface of at least the molding and filling portion chamber and the sealing portion chamber, and the aseptic air supplying apparatus supplies aseptic air into at least the molding and filling portion chamber and the sealing portion chambers, the molding and filling portion includes at least a mold, a blow nozzle, an extension rod, a valve block and a pressure apparatus that pressurizes the content from 1 MPa to 4 MPa, a cup-shaped closure apparatus is provided for receiving a substance discharged from the blow nozzle, and a circulation path is provided from the cup-shaped closure apparatus to the pressure apparatus, the valve block, and the blow nozzle, and the circulation path is circulated with a cleaner or a hot water for cleaning and sterilizing of an interior of a piping for the contents.

16. The aseptic filling machine according to claim 15, wherein a cleaning apparatus is provided which cleans the interior of the molding and filling portion chamber and the sealing portion chamber.

17. The aseptic filling machine according to claim 15, wherein the molding and filling portion chamber includes a movable portion that holds the molding and filling portion and a fixed portion that shields the molding and filling portion from an outside air.

18. The aseptic filling machine according claim 15, wherein a sterilizing device for the preform in the pre-heating sterilizing portion is configured to do any one or more of contact of the preform with a sterilizer, irradiation of the preform with an electron beam, irradiation of the preform with light containing ultraviolet radiation, contact of the preform with hot water, and contact of the preform with overheated vapor.

19. The aseptic filling machine according to claim 15, wherein a sterilizing device for the preform in the post-heating sterilizing portion is configured to do any one or more of contact of the preform with a gas or mist of a sterilizer or a mixture thereof, irradiation of the preform with an electron beam, irradiation of the preform with light containing ultraviolet radiation, and contact of the preform with overheated vapor.

20. The aseptic filling machine according to claim 15, wherein the pressure apparatus is a high-pressure plunger pump.

21. The aseptic filling machine according to claim 15, wherein an extension rod shielding chamber that shields the extension rod is provided.

22. The aseptic filling machine according to claim 15, wherein an extension rod driving apparatus is provided which drives the extension rod to a position where the extension rod is not inserted in the blow nozzle.

23. An aseptic filling method, comprising a pre-heating sterilization step of sterilizing a preform, a heating step of heating the sterilized preform, a molding and filling step of filling the heated preform with a sterilized content under high pressure, thereby molding the preform into a bottle and at the same time filling the preform with the content, and a sealing step of sealing the bottle filled with the content, wherein an interior and an inner surface of at least a chamber that shields from outside a portion in which the molding and filling step is performed and a chamber that shields from outside a portion in which the sealing step is performed are sterilized, aseptic air is supplied into the chambers, an aseptic condition is maintained in the chambers, and at least the molding and filling step and the sealing step are performed in the respective chambers in which the aseptic condition is maintained, before the aseptic filling machine starts operating, a blow nozzle is closed by a cup-shaped closure apparatus for receiving a discharged substance, a circulation path is provided from the cup-shaped closure apparatus to a pressure apparatus that pressurizes the content from 1 MPa to 4 MPa, a valve block, and a blow nozzle, and cleaning and sterilizing of an interior of a piping for the contents are performed by circulating a cleaner or a hot water in the circulation path.

24. The aseptic filling method according to claim 23, wherein before the interior and the inner surface of the chambers in which the molding and filling step and the sealing step are performed are sterilized, the interior and the inner surface of the chambers are cleaned.

25. The aseptic filling method according to claim 23, wherein the pre-heating sterilization step is achieved by any one or more of contact of the preform with a sterilizer, irradiation of the preform with an electron beam, irradiation of the preform with light containing ultraviolet radiation, contact of the preform with hot water, and contact of the preform with overheated vapor.

26. The aseptic filling method according to claim 23, wherein the molding and filling step includes connecting a blow nozzle to a top of a mouth portion of the sterilized and heated preform, closing a mold, expanding the preform in a lengthwise direction with an extension rod and then introducing the content pressurized into the preform under the control of a valve block, expanding the preform in a crosswise direction to mold the preform into the bottle having a shape of the mold, and at the same time filling the preform with the content to close to a lower end of the mouth portion of the preform.

27. The aseptic filling method according to claim 26, wherein the interior of the chamber in which the molding and filling step is performed is sterilized in a state where the extension rod is not inserted in the blow nozzle.

28. The aseptic filling method according to claim 26, wherein the interior of the chamber in which the molding and filling step is performed is cleaned in a state where the extension rod is not inserted in the blow nozzle.

29. The aseptic filling method according to claim 26, wherein the interior of the chamber in which the molding and filling step is performed is sterilized with a gas or mist of hydrogen peroxide or a mixture thereof in a state where a temperature of an outer surface of the blow nozzle is equal to or higher than 60° C. as a result of a flow path in the blow nozzle being cleaned or sterilized.

30. The aseptic filling method according to claim 26, wherein an inner surface of the mold is cleaned in a state where the mold is open while the mold is being rotated at a speed equal to or lower than 60 rpm.

31. An aseptic filling method, comprising a heating step of heating a preform, a post-heating sterilization step of sterilizing the heated preform, a molding and filling step of filling the sterilized preform with a sterilized content under high pressure, thereby molding the preform into a bottle and at the same time filling the bottle with the content, and a sealing step of sealing the bottle filled with the content, wherein an interior and an inner surface of a chamber that shields from outside a portion in which the molding and filling step is performed and a chamber that shields from outside a portion in which the sealing step is performed are sterilized, aseptic air is supplied into the chambers, an aseptic condition is maintained in the chambers, and the molding and filling step and the sealing step are performed in the respective chambers in which the aseptic condition is maintained, before the aseptic filling machine starts operating, a blow nozzle is closed by a cup-shaped closure apparatus for receiving a discharged substance, a circulation path is provided from the cup-shaped closure apparatus to a pressure apparatus that pressurizes the content from 1 MPa to 4 MPa, a valve block, and a blow nozzle, and cleaning and sterilizing of an interior of a piping for the contents are performed by circulating a cleaner or a hot water in the circulation path.

32. The aseptic filling method according to claim 31, wherein the post-heating sterilization step is achieved by any one or more of contact of the preform with a gas or mist of a sterilizer or a mixture thereof, irradiation of the preform with an electron beam, irradiation of the preform with light containing ultraviolet radiation, and contact of the preform with overheated vapor.

33. The aseptic filling method according to claim 31, wherein before the interior and the inner surface of the chambers in which the molding and filling step and the sealing step are performed are sterilized, the interior and the inner surface of the chambers are cleaned.

34. The aseptic filling method according to claim 31, wherein the molding and filling step includes connecting a blow nozzle to a top of a mouth portion of the sterilized and heated preform, closing a mold, expanding the preform in a lengthwise direction with an extension rod and then introducing the content pressurized into the preform under the control of a valve block, expanding the preform in a crosswise direction to mold the preform into the bottle having a shape of the mold, and at the same time filling the preform with the content to close to a lower end of the mouth portion of the preform.

35. The aseptic filling method according to claim 34, wherein the interior of the chamber in which the molding and filling step is performed is sterilized in a state where the extension rod is not inserted in the blow nozzle.

36. The aseptic filling method according to claim 34, wherein the interior of the chamber in which the molding and filling step is performed is cleaned in a state where the extension rod is not inserted in the blow nozzle.

37. The aseptic filling method according to claim 34, wherein the interior of the chamber in which the molding and filling step is performed is sterilized with a gas or mist of hydrogen peroxide or a mixture thereof in a state where a temperature of an outer surface of the blow nozzle is equal to or higher than 60° C. as a result of a flow path in the blow nozzle being cleaned or sterilized.

38. The aseptic filling method according to claim 34, wherein an inner surface of the mold is cleaned in a state where the mold is open while the mold is being rotated at a speed equal to or lower than 60 rpm.

39. An aseptic filling method, comprising a pre-heating sterilization step of sterilizing a preform, a heating step of heating the preform, a post-heating sterilizing step of sterilizing the heated preform, a molding and filling step of filling the sterilized preform with a sterilized content under high pressure, thereby molding the preform into a bottle and at the same time filling the preform with the content, and a sealing step of sealing the bottle filled with the content, wherein an interior and an inner surface of a chamber that shields from outside a portion in which the molding and filling step is performed and a chamber that shields from outside a portion in which the sealing step is performed are sterilized, aseptic air is supplied into the chambers, an aseptic condition is maintained in the chambers, and the molding and filling step and the sealing step are performed in the respective chambers in which the aseptic condition is maintained, before the aseptic filling machine starts operating, a blow nozzle is closed by a cup-shaped closure apparatus for receiving a discharged substance, a circulation path is provided from the cup-shaped closure apparatus to a pressure apparatus that pressurizes the content from 1 MPa to 4 MPa, a valve block, and a blow nozzle, and cleaning and sterilizing of an interior of a piping for the contents are performed by circulating a cleaner or a hot water in the circulation path.

40. The aseptic filling method according to claim 39, wherein before the interior and the inner surface of the chambers in which the molding and filling step and the sealing step are performed are sterilized, the interior and the inner surface of the chambers are cleaned.

41. The aseptic filling method according to claim 39, wherein the pre-heating sterilization step is achieved by any one or more of contact of the preform with a sterilizer, irradiation of the preform with an electron beam, irradiation of the preform with light containing ultraviolet radiation, contact of the preform with hot water, and contact of the preform with overheated vapor.

42. The aseptic filling method according to claim 39, wherein the post-heating sterilization step is achieved by any one or more of contact of the preform with a gas or mist of a sterilizer or a mixture thereof, irradiation of the preform with an electron beam, irradiation of the preform with light containing ultraviolet radiation, and contact of the preform with overheated vapor.

43. The aseptic filling method according to claim 39, wherein the molding and filling step includes connecting a blow nozzle to a top of a mouth portion of the sterilized and heated preform, closing a mold, expanding the preform in a lengthwise direction with an extension rod and then introducing the content pressurized into the preform under the control of a valve block, expanding the preform in a crosswise direction to mold the preform into the bottle having a shape of the mold, and at the same time filling the preform with the content to close to a lower end of the mouth portion of the preform.

44. The aseptic filling method according to claim 43, wherein the interior of the chamber in which the molding and filling step is performed is sterilized in a state where the extension rod is not inserted in the blow nozzle.

45. The aseptic filling method according to claim 43, wherein the interior of the chamber in which the molding and filling step is performed is cleaned in a state where the extension rod is not inserted in the blow nozzle.

46. The aseptic filling method according to claim 43, wherein the interior of the chamber in which the molding and filling step is performed is sterilized with a gas or mist of hydrogen peroxide or a mixture thereof in a state where a temperature of an outer surface of the blow nozzle is equal to or higher than 60° C. as a result of a flow path in the blow nozzle being cleaned or sterilized.

47. The aseptic filling method according to claim 43, wherein an inner surface of the mold is cleaned in a state where the mold is open while the mold is being rotated at a speed equal to or lower than 60 rpm.

* * * * *